(12) United States Patent
Evans et al.

(10) Patent No.: US 8,010,717 B2
(45) Date of Patent: *Aug. 30, 2011

(54) METHOD AND SYSTEM FOR COMMUNICATION AND COLLABORATION BETWEEN A PATIENT AND HEALTHCARE PROFESSIONAL

(75) Inventors: Junius Evans, Carlsbad, CA (US); Daniel Pettus, Carlsbad, CA (US); Rose Higgins, Washington Crossing, PA (US)

(73) Assignee: Imetribus, Inc., Mountain View, CA (US)

( * ) Notice: Subject to any disclaimer, the term of this patent is extended or adjusted under 35 U.S.C. 154(b) by 1488 days.

This patent is subject to a terminal disclaimer.

(21) Appl. No.: 10/417,794

(22) Filed: Apr. 17, 2003

(65) Prior Publication Data
US 2004/0210458 A1    Oct. 21, 2004

(51) Int. Cl.
*G06F 3/00*    (2006.01)
*G06Q 50/00*   (2006.01)
*A61B 5/00*    (2006.01)

(52) U.S. Cl. ............. 710/16; 705/2; 705/3; 710/15; 600/300

(58) Field of Classification Search ........... 705/2, 3; 600/300; 710/15–16
See application file for complete search history.

(56) References Cited

U.S. PATENT DOCUMENTS

| 5,948,077  | A  | * | 9/1999 | Choi et al. ............... 710/9 |
| 6,277,071  | B1 | * | 8/2001 | Hennessy et al. ........ 600/300 |
| 6,941,271  | B1 | * | 9/2005 | Soong .................... 705/3 |
| 7,016,726  | B1 | * | 3/2006 | Picardo et al. ........... 607/5 |
| 7,375,647  | B2 | * | 5/2008 | Evans et al. ............ 340/9.1 |
| 2002/0019749 | A1 | * | 2/2002 | Becker et al. ........... 705/2 |
| 2002/0082480 | A1 | * | 6/2002 | Riff et al. .............. 600/300 |

FOREIGN PATENT DOCUMENTS
EP    1800597 A2 *  6/2007

OTHER PUBLICATIONS

PR Newswire. "iMetrikus Announces MetrikLink" PR Newswire. New York: Nov. 5, 2001. p. 1.*

* cited by examiner

*Primary Examiner* — Dilek B Cobanoglu
*Assistant Examiner* — Anita Molina
(74) *Attorney, Agent, or Firm* — Dennis A. Bennett; Andrew Cubitt

(57) ABSTRACT

Methods and platforms for enhancing collaboration and communication between a patient and his healthcare team are described. A personal health record is created for a patient and maintained by a service provider. The health record is updated with self-monitored or remote device readings. These readings are sent, in a secure format that insures patient privacy, to the service provider and inserted into a health record via a computer connected to the Internet or via a telephone line without the use of a computer, i.e., by directly connecting an intermediate device to a phone outlet. Other health and wellness data may be written to the health record via a computer or via conventional means. By enhancing collaboration between patients and their healthcare teams, patients are more likely to improve their health conditions, particularly chronic conditions, and reduce healthcare costs.

13 Claims, 19 Drawing Sheets

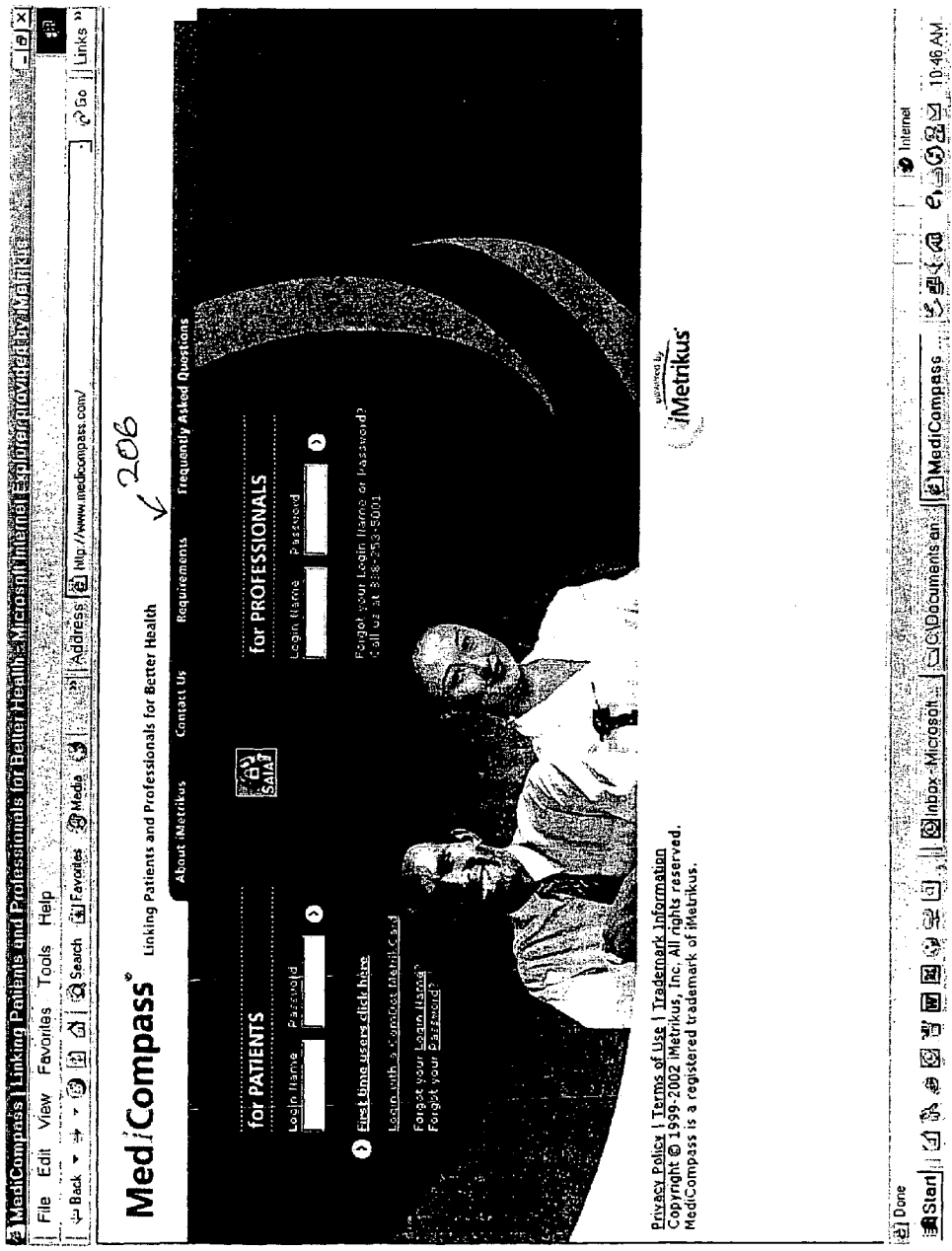

FIG. 2B

Med:Compass

ThePhysicianCenter — 208

Patients | Analyze | Educate | Connect | Options

Help    Logout

Today's Date: 8/20/2002
Your Last Visit Was: 8/15/2002

What You Should Know!

How to Navigate
- MediCompass Workspace
- Patients - Manage your list of patients
- Analyze - Review aggregate data on your patients
- Educate - Access patient and self-education resources
- Connect - Participate in chats and bulletin boards
- Options - Customize your preferences ▸ Patient Record
  Patient Profile - One page summary of recent data
  Record - Enter patient health information
  Graph - View/print graphs of the patient's data
  Reports - View/print reports of the patient's data

New and Notable

- Effective May 24, 2002, MediCompass and MyHealthChannel (for patients) will undergo the changes outlined below.

- MyHealthChannel will become MediCompass for Patients. In the future, current MyHealthChannel users and health professionals who use MediCompass will login at the same login page at www.MediCompass.com. The login page will also have a new look to streamline the login process.

- MediCompass channels for Physicians, Nurses, Pharmacists, Educators and Case Managers are being consolidated into one channel - MediCompass for Professionals.

- Free registration will no longer be available to patients or individual health professionals. Instead, access to our sites will only be available through programs offered by iMetrikus partner organizations.

Health News

▸ American Bar Association To Vote To Support Therapeutic Cloning (08/12/02)

▸ Stem Cell Implants Could Create New Blood Vessels, Save Limbs (08/09/02)

▸ Liposuction As Possible Treatment (08/09/02)

▸ New Insulin Gene Discovered (08/07/02)

HealthSense

Depression, A Frequently Overlooked Disease (August 8, 2002)
According to the members of the US Preventive Services Task Force depression is being missed in about half of adult Americans. It is felt this is because health care providers fail to address mental health issues during routine examinations. Although there are several formal depression-screening tools available, the task force found that asking two simple questions might be just as effective. Learn more.

Painless Drug Delivery: The Skin (July 23, 2002)
More and more medications can now be administered by a method of skin absorption called transdermal. Transdermal systems release medications into the blood stream through the skin. These patch systems commonly are used to deliver pain medications, male and female hormones, and smoking cessation patches. Learn more.

ADA Clinical Practice Recommendations 2001

- Home Diagnostics, Inc.
- Diabetes Testing Products
- Learn about the Prestige Smart System™

The Diabetes Mall

• Diabetes Guidelines
• Diabetes Web Resources

Next Page -->

Med:Compass

Nortina, Marguerite 54 y/o F  + Allergies

Patient Profile | Record | Graphs | Reports

Last Viewed: 8/9/2002    Record Key Status: Accepted    Demo Tools    Help    Close Today's Date: 8/20/2002
Last Patient Login: 8/15/2002

Condition Being Monitored: Diabetes Mellitus Type 1
Date of Diagnosis: 11/21/2001
DOB: 2/28/1948

Drug Allergies
penicillin G

Non-Drug Allergies
animals
environmental
hay fever

Vitals

| Date | Test | Value |
|---|---|---|
| 3/9/2000 | Temperature | 98.60 F |
| 8/8/2002 | Heart Rate | 82 |
| 8/8/2002 | Blood Pressure | 114/78 |
| 8/8/2002 | Height | |
| 8/8/2002 | Weight | 0.0 lbs |
| 8/8/2002 | BMI | |
| 4/9/2002 | Feel Good Score | 8 |
| 5/28/2001 | Stress Level | 1 |

HbA1c (12 months)

| Date | Result |
|---|---|
| 7/11/2002 | 8.7 |
| 7/2/2002 | 9.0 |
| 6/16/2002 | 8.3 |
| 5/9/2002 | 8.1 |
| 3/1/2002 | 8.4 |
| 12/21/2001 | 8.7 |
| 10/30/2001 | 8.3 |
| 8/23/2001 | 9 |

Last Exams

| Date | Exam | Result |
|---|---|---|
| 6/7/2002 | Diabetic Retinal Exam | Normal |
| 8/5/2002 | Foot Exam | Normal |
| | Dental Exam | |

Self-Monitored Glucose Results (Last 24 Hours)

| Date | Time Slot | Glucose |
|---|---|---|

Labs

| Date | Type | Result |
|---|---|---|
| 4/2/2002 | Cholesterol level | 204 |
| 7/10/2002 | LDL cholesterol | 106 |
| 7/10/2002 | HDL cholesterol | 40 |
| 3/26/2001 | Triglycerides | 231 |
| | Urine Protein | |
| 6/7/2002 | Microalbumin, spot urine | Normal |
| | Microalbumin/Creatinine Ratio | |

Active Medications

| Start Date | Medication |
|---|---|
| 6/15/2002 | Glucophage 500 mg, 4 tablet, bid |
| 10/2/2001 | combivir, 150/300 mcg, bid |
| 10/2/2001 | didanosine, 125 mcg, bid |
| 5/28/2001 | vitamin C, 2 capsule, hs |
| 4/3/2001 | Serevent, 2 puff, bid |
| 12/7/2000 | warfarin, 10 mg, qAM |
| 2/8/2000 | glucosamine, 500 mg, tid |
| 8/2/2000 | Lipitor, 10 mg, qd |
| 1/1/1995 | Calcium Caltrate, 1000 mg, qd |
| 1/1/1995 | multivitamin, 1 tablet, qd |

ADA Clinical Practice Recommendations 2001

Advance Directives
click for more info

Search for:

amazon

Next Page -->

FIG. 2E

MediCompass

Nortina, Marquerite    54 y/o F

| Date | Time | Result | Unit | Time Slot | Event | Source |
|---|---|---|---|---|---|---|
| 8/6/2002 | 9:53:00 PM | 225 | mg/dL | Bedtime | | |
| 8/6/2002 | 7:17:00 PM | 114 | mg/dL | After Dinner | | |
| 8/6/2002 | 6:21:00 PM | 88 | mg/dL | Before Dinner | | |
| 8/6/2002 | 12:51:00 PM | 105 | mg/dL | After Lunch | | |
| 8/6/2002 | 11:48:00 AM | 111 | mg/dL | Before Lunch | | |
| 8/6/2002 | 8:19:00 AM | 133 | mg/dL | After Breakfast | | |
| 8/6/2002 | 7:17:00 AM | 121 | mg/dL | Before Breakfast | | |
| 8/5/2002 | 9:53:00 PM | 141 | mg/dL | Bedtime | | |
| 8/5/2002 | 7:17:00 PM | 155 | mg/dL | After Dinner | | |
| 8/5/2002 | 6:21:00 PM | 121 | mg/dL | Before Dinner | | |
| 8/5/2002 | 12:51:00 PM | 143 | mg/dL | After Lunch | | |
| 8/5/2002 | 11:48:00 AM | 55 | mg/dL | Before Lunch | | |
| 8/5/2002 | 10:59 AM | 23 | mg/dL | Before Lunch | | |

Date*:
Time (hh:mm am/pm)*:
Result*:
Unit*: mg/dL
Time Slot*:
Event:
Comment:

Upload    Save New    Undo

FIG. 3A

Med:Compass  300

MyHealthCenter | Record | Graphs | Reports | Learn | Connect | Demo Tools | Shop

MyHealthCenter  Preferences  Help  Logout

Congratulations imetdB3! This is visit 290.
By tracking your health regularly, you will understand how you can feel better!

Today's Date: 8/20/2002
Your Last Visit Was: 8/9/2002

My Health News
- American Bar Association To Vote To Support Therapeutic Cloning (08/12/02)
- Stem Cell Implants Could Create New Blood Vessels, Save Limbs (08/09/02)
- Liposuction As Possible Treatment (08/09/02)
- New Insulin Gene Discovered (08/07/02)

What You Should Do Today!
1. View your MetriKList tasks and record the results.
2. Upload Your Blood Pressure and Heart Rate Readings.
3. Measure and RECORD your glucose (blood sugar) levels on MyHealthChannel.
4. Call your healthcare professional to schedule your necessary tests which may include:
   - HbA1c
   - BUN and Creatinine tests
   - Creatinine Clearance
   - Microalbuminuria
   - Coronary Risk Profile
   - Retinal Exam
   - Diabetic Foot Exam
5. Be sure to RECORD your results under "Lab Tests" for future reference!
6. Print graphs and reports of your blood sugar information for healthcare professional appointments.

New and Notable
- Automatically upload your data! New glucose meters and now an insulin pump supported:
  - D-TRON Insulin Pump
  - Prestige Smart System, One Touch Ultra, and FreeStyle glucose meters
- Get connected! Once you Get a Cable, you'll be able to upload information from your insulin pump or blood glucose meter.

*HealthSense*

Depression, A Frequently Overlooked Disease (August 8, 2002)
According to the members of the US Preventive Services Task Force depression is being missed in about half of adult Americans. It is felt this is because health care providers fail to address mental health issues during routine examinations. Although there are several formal depression-screening tools available, the task force found that asking two simple questions might be just as effective. Learn more...

Painless Drug Delivery: The Skin (July 23, 2002)
More and more medications can now be administered by a method of skin absorption called transdermal. Transdermal systems release medications into the blood stream through the skin. These patch systems commonly are used to deliver pain medications, male and female hormones, and smoking cessation patches. Learn more...

TWIN TOWERS FUND
NABCO
Search for: amazon

- Diabetes Guidelines
- Resources for Diabetes
- Rewards for Managing Your Diabetes Next Page -->

FIG. 3B

MediCompass

MyHealthCenter | Record | Graphs | Reports | Demo Tools | | |
Connect | Learn | Shop | Preferences | Help | Logout Today's Date: 8/20/2002
Your Last Visit Was: 8/9/2002

MyHealthCenter

Congratulations imetdb3! This is visit 290.
By tracking your health regularly, you will understand how you can feel better!

What You Should Do Today!

1. View your Metriklist tasks and record the results.
2. Upload Your Blood Pressure and Hea
3. Measure and RECORD your glucose (
4. Call your healthcare professional to
   - HbA1c
   - BUN and Creatinine tests
   - Creatinine Clearance
   - Microalbuminuria
   - Coronary Risk Profile
   - Retinal Exam
   - Diabetic Foot Exam
5. Be sure to RECORD your results un
6. Print graphs and reports of your bloc appointments.

New and Notable

- Automatically upload your data! New glucose meters and now an insulin pump supported:
  - D-TRON Insulin Pump
  - Prestige Smart System, One Touch Ultra, and FreeStyle glucose meters
- Get connected! Once you Get A Cable, you'll be able to upload information from your Insulin pump or blood glucose meter.

---

Upload Data - Microsoft Internet Explorer

MediCompass

Select glucose meter or insulin pump for upload:

[ D-TRON Pump ▼ ]

[ OK ]  [ Cancel ]

☐ Do not show me this at login. (Access the Preferences link on the top of the main window to resume login prompting.)

---

My Health News

- American Bar Association To Vote To Support Therapeutic Cloning (08/12/02)
- Stem Cell Implants Could Create New Blood Vessels, Save Limbs (08/02/02)

*thSense*

A Frequently ed Disease (August 8, to the members of the US a Services Task Force n is being missed in about ult Americans. It is felt this e health care providers fail s mental health issues tine examinations. there are several formal n-screening tools the task force found that o simple questions might be just as effective. Learn more...

Painless Drug Delivery: The Skin (July 23, 2002)
More and more medications can now be administered by a method of skin absorption called transdermal. Transdermal systems release medications into the blood stream through the skin. These patch systems commonly are used to deliver pain medications, male and female hormones, and smoking cessation patches. Learn more...

---

TWIN FUND TOWERS
Click Here to Donate

Search for:
amazon [Go]

- Diabetes Guidelines
- Resources for Diabetes
- Rewards for Managing Your Diabetes!

Next Page -->

METHOD AND SYSTEM FOR COMMUNICATION AND COLLABORATION BETWEEN A PATIENT AND HEALTHCARE PROFESSIONAL

BACKGROUND OF THE INVENTION

1. Field of the Invention

The present invention relates generally to methods and computer systems for communication between healthcare consumers and healthcare professionals and for managing a healthcare consumer's personal health data. More specifically, the present invention relates to chronic care informatics and to methods and systems encouraging self-management and tools to monitor compliance. In addition, the invention relates to methods for allowing a patient to collaborate with a professional regarding the monitoring and treatment of the patient's chronic health condition, general health and wellness via a computer network.

2. Discussion of Related Art

There are presently numerous devices available to a healthcare consumer, referred to generally as "patient," for monitoring health conditions at home or other remote locations, such as a patient's workplace or home. Healthcare professionals include doctors, nurses, homecare providers, clinicians, pharmacists, and so on, and are hereinafter collectively referred to as "doctor" or "professional." Remote monitoring has been one of the more important new practices advocated by the healthcare industry for reducing healthcare costs.

Recently, healthcare costs, including treatment and medication, have been rising at alarming rates for all demographic groups. One illustration of this is recent findings that consumer prices of generic drugs are rising at a faster rate than the prices of brand name drugs. One approach widely recognized for reducing these costs is to improve ways for patients, particularly those with chronic conditions, to collaborate with their doctors and, generally, get more involved in the treatment and monitoring of their own health conditions. One way this has been done is through self-monitoring of their conditions and communicating the data from self-monitoring devices to their doctors.

Monitoring various basic metrics, for example, blood glucose level, blood pressure, key lab tests, medications, and other measurements by a patient outside a doctor's office gives the patient the opportunity to better understand and improve his condition while reducing costs and inefficiencies resulting from frequent office visits. Using diabetes as an example, one type of home healthcare monitoring that has experienced widespread use among diabetes patients is the remote measuring of blood glucose levels, also known as blood sugar. There are several different types of self-monitoring meters for measuring blood glucose and related independent software needed for downloading readings for analysis by a doctor.

Readings and measurements collected by a self-monitoring device are often downloaded by the doctor during a patient visit for analysis and retention in a database. However, although the advantage of self-monitoring devices are widely recognized, the market for such health devices and associated software has become disparate and incompatible. This has created a problem at the doctor's end where the doctor typically has to maintain multiple incompatible software and hardware interfaces to accommodate the various monitoring devices used by patients. The software and interface incompatibility has also led to doctors not being able to uniformly store measurement data from different devices in a uniform or single repository. Furthermore, patients may not have access to a computer or the appropriate software to allow them to use the data to manage their condition or to have collaborative discussions about the data with their doctors.

Therefore, it would be beneficial to patients, doctors, and other entities in the healthcare industry, to facilitate and standardize the processes of obtaining, transmitting, processing, and storing data from self-monitoring measuring devices. For example, for many patients, an improvement would be to use only a telephone outlet rather than a computer to transmit data to a doctor or other healthcare provider. Furthermore, in cases where the patient is using more than one type of self-monitoring device, it would be beneficial if all the devices were compatible with an intermediate, data-linking device that performed as a common interface or data conduit for transmitting data over a telephone line or network. It would also be beneficial to patients and other entities if a patient could effectively transmit data to additional healthcare professionals, such as nurses or pharmacists, wherein these individuals are authorized to access the patient data and work with the patient's primary care physician in managing the patient's condition. Therefore, it is beneficial to have a common, comprehensive database capable of receiving downloaded information from all devices without respect to proprietary restrictions. Furthermore, it is important that the sharing of access to this personal health data be controlled by the patient at all times.

From the doctor's perspective, it would be greatly beneficial to have access to a common central data repository storing all his patients' personal healthcare data. In addition, accessing a personal health data repository and processing engine should be secure, efficient and cost-effective for the doctor, the patient and other professionals. It would also be desirable to encourage participation by the doctor, patient, and other entities in the healthcare industry, such as pharmaceutical, life science, and health insurance companies, in actively utilizing a system and network in which patients and doctors benefit. A significant benefit of a common, comprehensive database to the doctor and generally to the healthcare industry would be the availability of depersonalized aggregate analysis of the data to study trends across patient populations based on disease, demographics, or other stored parameters. Finally, it would be desirable to better educate the patient and provide more frequent instructions and guidance from doctors regarding a patient's specific health conditions and goals, thereby enabling the patient to be more effective in improving his health condition.

SUMMARY OF THE INVENTION

Methods and platforms for enhancing collaboration and communication between a patient and his healthcare team are described. A personal health record is created for a patient and maintained by a health data management service provider. The health record is updated with self-monitoring device readings. These readings are sent to the service provider and inserted into a health record via a computer connected to the Internet or via a telephone line without the use of a computer, i.e., by directly connecting an intermediate data linking device to a phone outlet. Other health and wellness data may be written to a health record via a computer or via conventional means. Personal health records are created with minimal effort from healthcare professionals and patients. Third-party companies in the healthcare industry, such as insurance companies and pharmaceutical companies, sponsors a program encouraging the creation of personal health records. By enhancing collaboration between patients and their healthcare teams, patients are more likely to improve their health conditions, particularly chronic conditions, and reduce healthcare costs.

BRIEF DESCRIPTION OF THE DRAWINGS

The invention will be better understood by reference to the following description taken in conjunction with the accompanying drawings in which:

FIG. 2A is a screen display of a login page of an online chronic care data management program in accordance with one embodiment of the present invention.

FIG. 2B is a screen display showing a healthcare professional's initial screen in accordance with one embodiment of the present invention.

FIG. 2C is a screen display showing a list of patients from which a healthcare professional can select a patient after selecting a "Patients" tab shown in the screen display of FIG. 2B.

FIG. 2D is a screen display showing a summary of the information from a personal health record, referred to as a Patient Profile or Face Sheet page, after selecting "View Record" for a record in the screen display of FIG. 2C.

FIG. 2E is a screen display showing a patient's meter readings from a glucose meter, including time, data, and time slot of when the reading was taken.

FIG. 3A is an initial screen display on the patient side of the online chronic care data management program in accordance with one embodiment of the present invention.

FIG. 3B is an initial screen display on the patient side as shown in FIG. 3A which allows a patient to select a self-monitoring device by a particular manufacturer.

DETAILED DESCRIPTION

Reference will now be made in detail to a preferred embodiment of the invention. An example of the preferred embodiment is illustrated in the accompanying drawings. While the invention will be described in conjunction with a preferred embodiment, it will be understood that it is not intended to limit the invention to one preferred embodiment. To the contrary, it is intended to cover alternatives, modifications, and equivalents as may be included within the spirit and scope of the invention as defined by the appended claims.

Methods and systems for enhancing collaboration and communication between patients and doctors for treating patients' health conditions are described in the various figures. The present invention is a novel platform for communication between a patient and doctor or other healthcare professional and is a novel form of storing and viewing clinical data as a patient health record. The novel platform of the present invention encourages and reinforces constructive self-management of health conditions, particularly chronic health conditions, and provides tools, including a data analysis engine to monitor compliance with treatment strategies. The present invention also encompasses novel methods of enrolling new members, such as patients and doctors and other members of a care team, into a network that is the underlying infrastructure of the new form of communication between a patient and members of his care team. The present invention further includes incentives and awards to patients and healthcare professionals for frequently using the new platform and network, thereby building robust personal health records that are rich with data.

Figure 1:
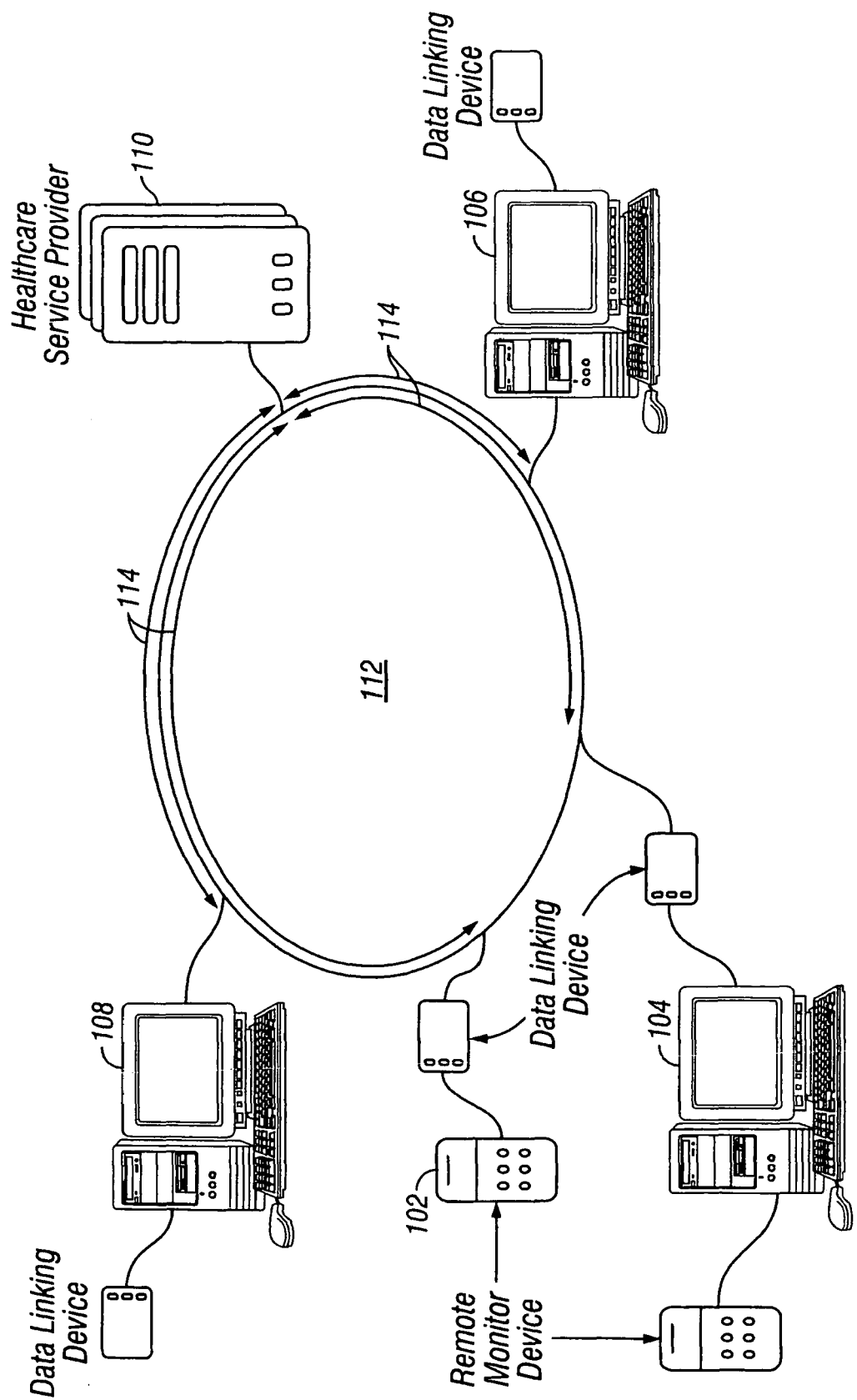
FIG. 1 is an overview diagram of various parties having a role in the present invention and of the flow of personal health record data among the parties in accordance with one embodiment of the present invention.

FIG. 1 is an overview diagram of various entities involved in the present invention and of the flow of personal health data among the entities in accordance with one embodiment of the present invention. Shown are patient equipment 102 (self-monitoring device and data linking device) and equipment 104 (devices and computer) at patients' homes or other remote locations; various healthcare professionals: doctor 106 and nurse 108 (other examples of healthcare professionals include clinician, educators, case managers, and pharmacists); and a healthcare data service provider 110 ("service provider"), such as assignee iMetrikus, Inc., operating numerous database servers, engines, and other components. In another preferred embodiment, other parties in the healthcare industry, such as pharmaceutical and insurance companies are connected to the network and are able to communicate with the service provider. All entities are connected digitally via a computer network 112, such as the Internet in the described embodiment. In other embodiments, a party may be connected to network 112 via a wireless protocol and may use any Internet appliance or Internet-enabled device.

Service provider 110 stores and processes personal health Data™ stored in a personal health Record™ described below. Generally, a personal health record contains a wide range of health and wellness data most of which is supplied by a patient. Specifically, the data includes measurements and readings from one or more remote or self-monitoring health devices such as a blood glucose meter and asthma monitor. Doctors and other healthcare professionals also supply data in a personal health record. In a preferred embodiment, a patient health record is accessible by the patient and by members of his healthcare team. In the described embodiment, data are transmitted between patients and healthcare professionals via healthcare data service provider 110. Data are stored to and retrieved from service provider 110 as shown by arrows 114 in FIG. 1. In the described embodiment, service provider 110 maintains structured and codified clinical repositories that store aggregated and longitudinal healthcare data.

In a preferred embodiment, a patient personal health record is stored or server computers under the control of service provider 110. Typically, data are transmitted from the patient, originating either directly from a self-monitoring device, that is, taking readings related to a patient's condition, or directly from the patient, e.g., text input regarding exercise, diet, medication, and so on. Personal health data are transmitted from patient sites 102 and 104 to servers maintained by service provider 110 via network 112, such as the Internet, a virtual private network (VPN), or other digital network, including wireless networks. Similarly, data are transmitted from professional sites 106 and 108 to service provider 110. As described in greater detail below, data relating to a patient from the various entities are stored in a personal health record comprised of a single file accessible by the patient and his healthcare team. In addition, certain portions of these data are provided to authorized third-parties, for example, to determine patient compliance with a treatment strategy.

In FIG. 1, in a preferred embodiment, data are not transmitted directly between a patient and his doctor, as shown by the arrows of FIG. 1. When a party accesses data, the data are retrieved directly from data repositories maintained by the service provider. Similarly, when data are pushed out to an entity, such as a patient, data (which may have originated from the doctor or other healthcare professional) are transmitted by the service provider from its repositories. Instructions to transmit or push data are likely to come from a healthcare professional, e.g., a prompt to a patient to take action on key health maintenance activities, notifying a patient of developments relating to his chronic condition, reminders and alerts to take a medication or schedule an office visit, and other personalized and targeted messages. As described in greater detail below, this can be done while allowing a doctor to examine a patient's responses between office visits.

Depending on access authorizations granted by the patient, a personal health record can be updated by other entities, in which case data are transmitted from an entity to the service provider where updates are made to personal health records. In a preferred embodiment, the data are secured on servers maintained by the service provider. Patients and healthcare professionals store and access data on the service provider's servers via an Internet website. In the described embodiment, the website is referred to as MediCompass® an online healthcare data management program.

In the described embodiment, the online channel used by patients and healthcare professionals to access a personal health record is the MediCompass® online healthcare data management program system, implemented in the described embodiment as a website. Through the MediCompass® online healthcare data management program website, a patient is able to view and update his personal health record, receive messages and information from his healthcare team, and access other relevant information. In the described embodiment, it is expected that many of the updates made to a personal health record will be in the form of measurements and readings from remote or self-monitoring health devices. However, a number of other types of updates can be made by patients and doctors. For example, a patient can enter information regarding diet, exercise, wellness, medication, and so on. The MediCompass® online healthcare data management program initial logon screen is the same for patients and healthcare professionals, and the underlying data views shown to various parties are similar. However, one inherent and obvious difference between the interfaces is the ability of a doctor to view a list of patient records whereas a patient can only view his own record. Other differences include menu options that are applicable either to patients or professionals. However the basic data, particularly data within a personal health record viewable by a patient and his healthcare team, are the same.

In the described embodiment, doctors use the MediCompass® online healthcare data management program website to access and update patients' personal health records. Through MediCompass® online healthcare data management program a doctor accesses a personal health record for a patient from a list of patients, each of whom has granted the doctor authorization to access their data. A patient has a list of healthcare professionals to whom the patient can send messages, data, and readings from self-monitoring devices. In the described embodiment, personal health records are stored in a secure MediCompass® online healthcare data management program database maintained by the service provider.

A patient shares health information with the service provider via MediCompass® online healthcare data management program over the Internet or other type of computer network. However, a patient can share health information with the service provider without having to access the website or without having to use a computer or other Internet-enabled device. A patient can upload meter readings from a self-monitoring device directly to the health record maintained by the service provider in a database over the Internet by connecting the device to an intermediate device as shown in equipment 102 of FIG. 1. The intermediate device is directly inserted into a telephone outlet. By simply pressing a button on the intermediate data linking device, data from the monitoring device is sent directly, in a secure and private manner, to the shared personal health record.

The patient can also connect the intermediate data linking device to a computer for transmitting data into the health record via the Internet rather than the telephone line. Healthcare professional offices, all of which will likely have a computer connected to the Internet, will also use MetrikLink® intermediate data linking device connected to their computer, described in patent application, commonly assigned, Ser. No. 09/977,472, filed on Oct. 15, 2001, titled "Method and System for Communicating Data Between a Medical Device and a Central Data Repository," incorporated herein for all purposes.

"To achieve the foregoing, methods and apparatus are disclosed for transmitting medical and health-related data from self-monitoring diagnostic devices via an intermediate device to a central server or data repository where the intermediate device is adaptable with numerous medical and health meters."
[U.S. Pat. No. 7,375,647 Summary of the Invention, column 2, lines 42-47].

Figure 7:
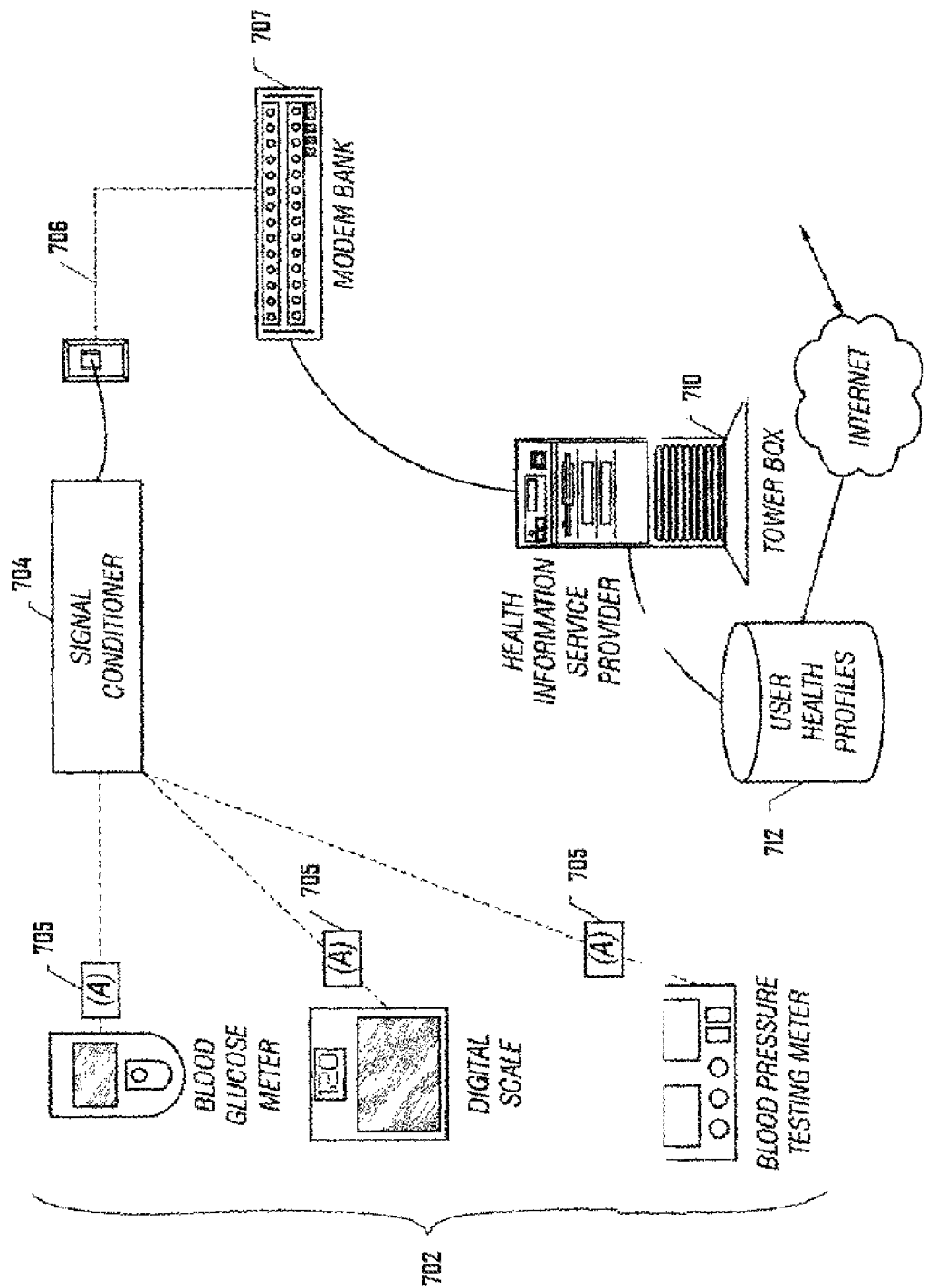
FIG. 7 is a block diagram of a configuration showing the context in which a signal conditioner is used in accordance with one embodiment of the present invention.

"In accordance with a preferred embodiment of the present invention, there is provided a signal conditioner capable of trafficking metric data between a variety of self-diagnosing devices and a health information service provider ("service provider"). The service provider controls an aggregate server that contains or controls a database that in turn contains user health profiles among other data. To further illustrate the foregoing, FIG. 7 is a block diagram of a configuration showing the context in which a signal conditioner is used in accordance with one embodiment of the present invention. A number of different types of self-diagnosing medical devices 702 can interface with a signal conditioner or interface appliance 704. Device-independent appliance 704 is described in greater detail in FIG. 8 below. A signal conditioner adaptor assembly 705 is used to connect various medical devices 702 to signal conditioner 704. Adaptor assembly 705 has a receptacle in which a device-specific adaptor is inserted. The receptacle is designed to accept any type of device adaptor associated with self-diagnosing medical devices 702. Each device 702 typically comes with its own adaptor that snaps into the receptacle and each device-specific adaptor has a specific resistance. The signal conditioner also has a specific resistance. As described below, identification of the device is done by using a voltage divider and analog detect schema. The voltage divider divides the device adaptor resistance by the signal conditioner resistance to produce an analog voltage. This voltage is sent to an analog/digital converter in signal conditioner 704, described below.

In a preferred embodiment, signal conditioner 704 connects to a telephone line 706 using an internal modem (not shown). Metric data is then transmitted via a standard telephone line to a modem bank 707 that connects to the service provider which parses the data before storing it in a database 712. Server 710 also contains intelligence and other information to configure signal conditioner 704 according to the type of device 702 to which it is connected.

Figure 8:
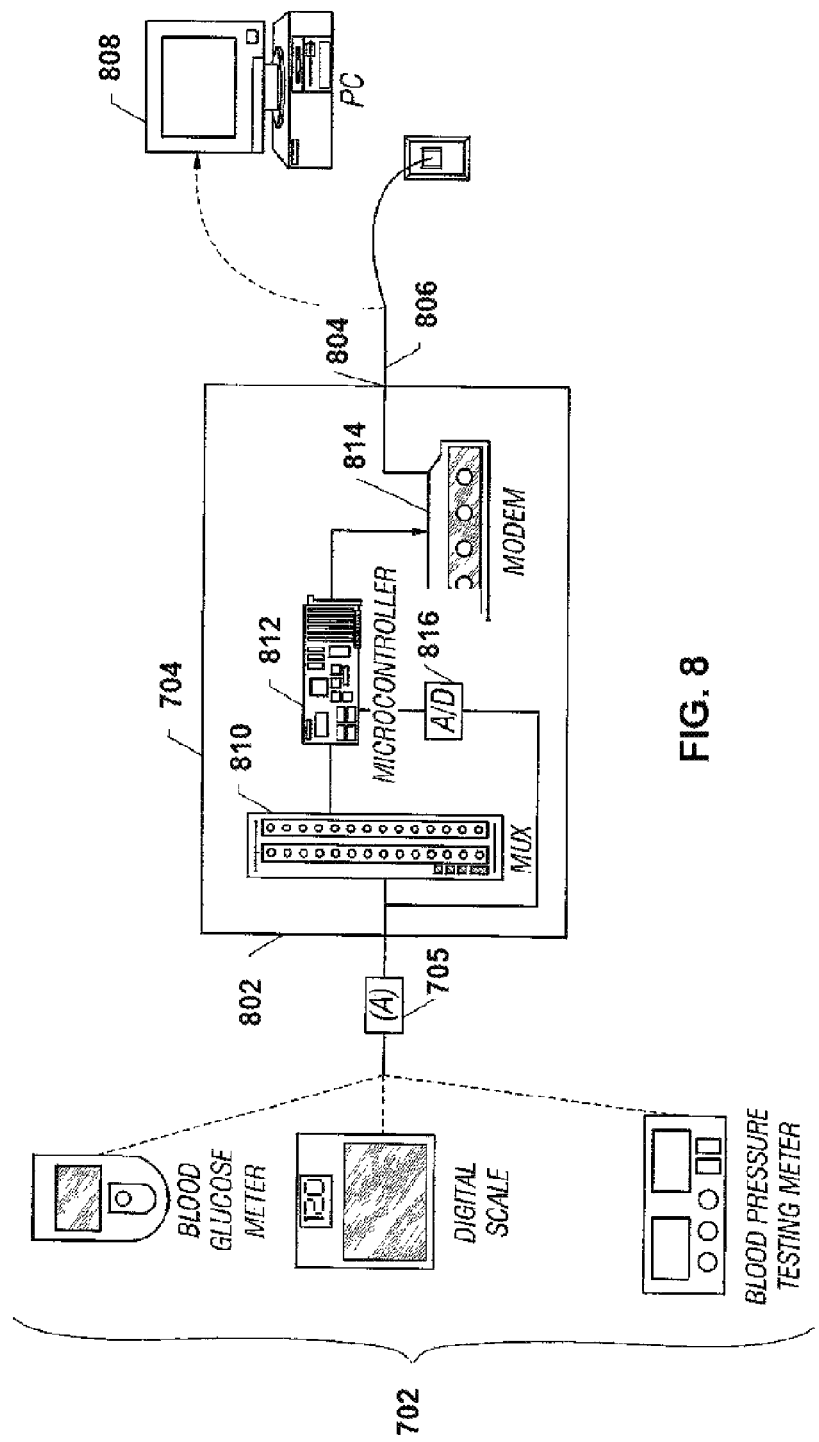
FIG. 8 is a block diagram of a signal conditioner capable of interfacing with numerous type of self-diagnosing medical devices on one end and a host device on the other in accordance with one embodiment of the present invention.

FIG. 8 is a block diagram of a signal conditioner capable of interfacing with numerous type of self-diagnosing medical devices on one end and a host device on the other in accordance with one embodiment of the present invention. A signal conditioner 704 shown in FIG. 7 has a self-diagnosing medical device I/O port 802 and a host I/O port 804. As described above, device I/O 802 can interface with numerous type of devices 702 having different interface standards and communication protocols via adaptor assembly 705. These include 5V TTL/CMOS, 3V TTL/CMOS, RS232, and IRDA. Host I/O 204 enables connections to a telephone jack 806 or to a PC 808. It is through host I/O 804 that data is communicated to and from a server under control of a service provider. In signal conditioner 704 are numerous components: a multiplexer (MUX) 810, a microcontroller 812, a modem 814; and an analog/digital converter 816, among other components not shown. MUX 810 is able to switch and communicate different voltage levels and signal levels (TTL, CMOS, RS232, or IRDA).

Signal conditioner 704 can be described as a configurable multiplexer in that all the various signal and voltage levels go through a single channel, thus a "configurable" multiplexer. Normally, the different levels would be handled by an equal number of channels. Signal conditioner 704 essentially transposes or repackages signals from various devices 702. In contrast to existing devices, signal conditioner 704 does not store or have embedded any intelligence or knowledge of devices 702 with which it can interface. This intelligence is kept on server 710 and is used to configure signal conditioner 704 according to the type of device to which it is connected. The functions of these components are described below with respect to the process that takes place with signal conditioner 704.

Figure 9:
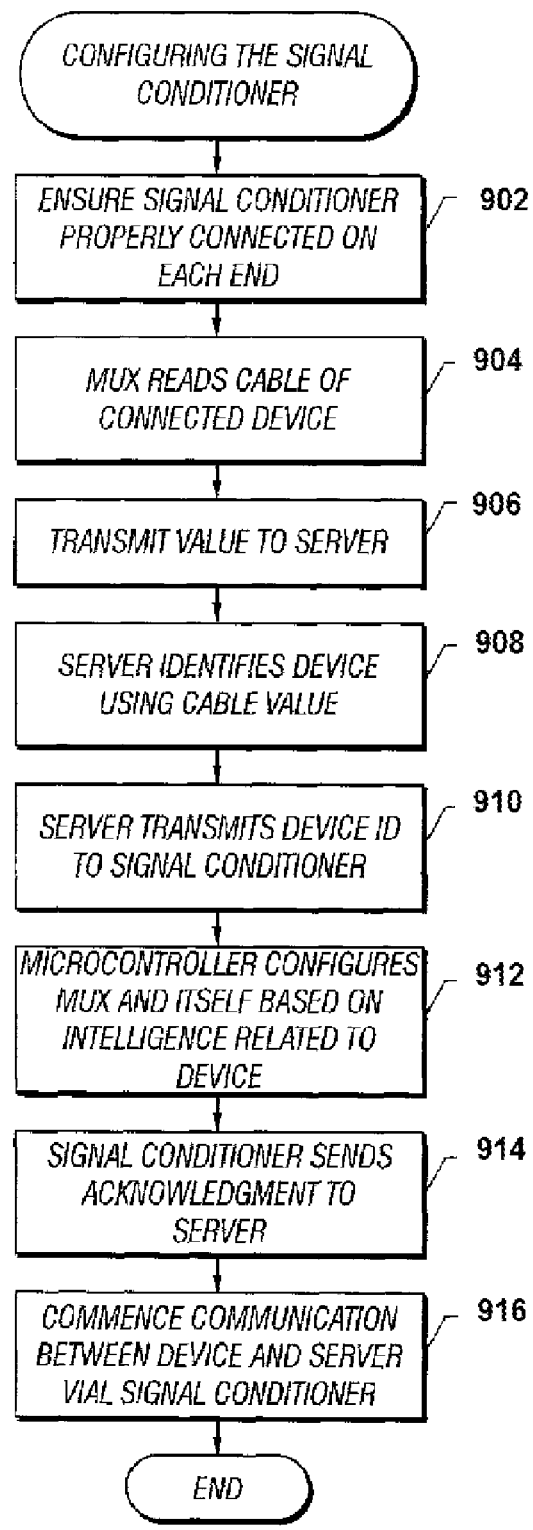
FIG. 9 is a flow diagram of a process of configuring the signal conditioner to communicate data between a particular self-monitoring medical device and a service provider in accordance with one embodiment of the present invention.

FIG. 9 is a flow diagram of a process of configuring the signal conditioner to communicate data between a particular self-monitoring medical device and a service provider in accordance with one embodiment of the present invention. In the preferred embodiment, the signal conditioner sends metric data directly through a dial-up modem via a standard public telephone switch network to a service provider server. As described above, the signal conditioner can also be used with a PC to access the Internet and communicate with the server. First, a health care consumer or healthcare-taker plugs in a self-monitoring device to the signal conditioner through device I/O port 802. Host I/O 804 is connected to a telephone line. At step 902 the signal conditioner determines whether it is properly connected on each side. If the device is not connected to the device I/O or the host I/O is not connected to a telephone line, it does not begin operation. The signal conditioner uses a series of LED indicators for each step of the upload operation. Both successful and error states are indicated using the LEDs. At step 904 the MUX reads the cable, represented by a particular value, that is plugged into the signal conditioner. This is described in greater detail in FIG. 10 below. Once a value representing the type of cable is determined, this value is transmitted to the server via the telephone line at step 906. Examples of device cable types are: ⅛"Audio Plug, 3/32"Audio Plug, Custom 3 PIN PCB, and Custom 3 PIN, among others.

The server at the service provider uses this value to identify the device connected to the signal conditioner at step 908. The signal conditioner identifies the attached device using a voltage divider schema. Basically a fixed resistor value is located on the signal conditioner main circuit board. Each device cable adaptor contains a unique resistor value. Dividing the voltage and obtaining the analog value determines the unique device connector to the signal conditioner. At step 910 a device identifier is sent to the signal conditioner. Specifically, microcontroller 912 receives the device ID at step 910. At step 912, the microcontroller switches the MUX to the appropriate output levels and configures itself to the appropriate bit rate. At step 914 the signal conditioner sends a positive acknowledgment to the server that it has received and processed the device ID. This acknowledgment can also be sent before switching the MUX or configuring the microcontroller. At step 916 communication begins between the device and the server via the signal conditioner. At this stage, metric data from the device is uploaded to the server and the process is complete. The amount of time this takes depends on various factors known in the field such as amount of data stored in memory and bit rate. As mentioned above, signal conditioner 704 does not keep any data regarding any of the dozens of devices with which it can interface. All the intelligence for configuring it is sent essentially on a 'need-to-know' basis from the server. One of the numerous advantages of this is that the signal conditioner is adaptable to future devices; all that needs to be done is to store intelligence for the new device on the service provider server.

Figure 10:
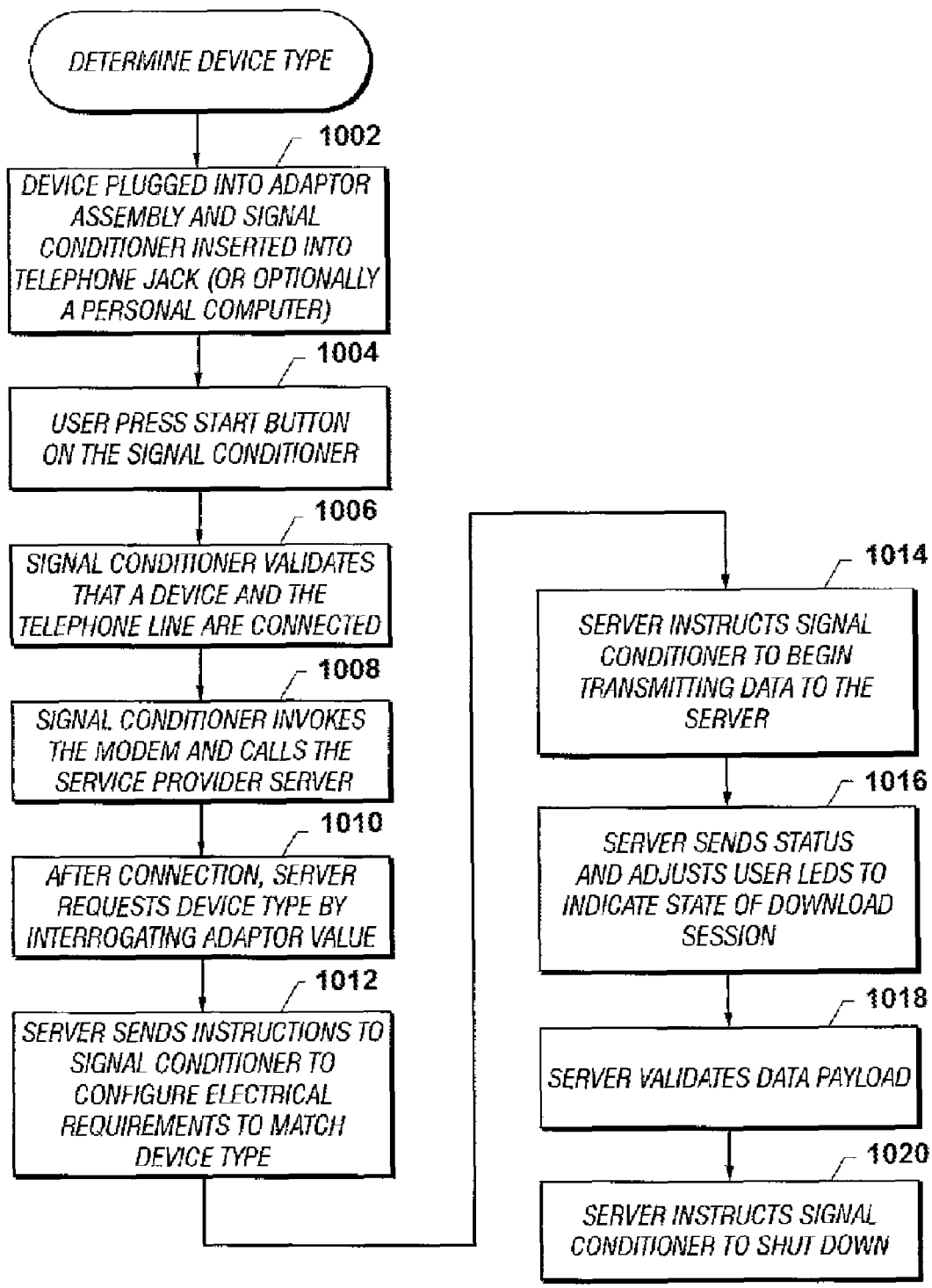
FIG. 10 is a flow diagram of a process of determining the type of cable connected to the signal conditioner in accordance with one embodiment of the present invention.

FIG. 10 is a flow diagram of a process of determining the type of cable connected to the signal conditioner in accordance with one embodiment of the present invention. It describes in greater detail a process by the signal conditioner in determining the type of cable connected to it from the device in step 904 above. At step 1002 the device adaptor is inserted into the adaptor assembly thereby allowing the adaptor assembly to plug into the device. The signal conditioner is plugged into a telephone jack or a personal computer. At step 1004 the user presses a START button on the signal conditioner. At step 1006 the signal conditioner validates that the device is connected to the signal conditioner via the adaptor assembly and that the signal conditioner is connected to a telephone jack. This is done once the two connections to the signal conditioner are in place. At step 1008 the signal conditioner invokes an internal modem 814 and dials into the service provider server. At this time a handshake is performed between the signal conditioner and the modem bank using known techniques.

Once a connection is established between the signal conditioner and the server, at step 1010 the server obtains the device type by interrogating an adaptor value. At step 1012 the server sends instructions to the signal conditioner to configure its electrical requirements to match the device type. This configuration can be according to RS232, 5 volt, 3 volt, and so on. At step 1014 the server instructs the signal conditioner to begin transmitting data from the device to the server. The server then parses the metric data from the self-monitoring device and stores it in a user health profile for the user in a database under control of the service provider. At step 1016 the server sends status data and adjusts LEDs on the signal conditioner to indicate the state of the download session. At step 1018 the server validates the data it received from the signal conditioner. At step 1020 the server instructs the signal conditioner to shut down and the connection is terminated.

Figure 11:
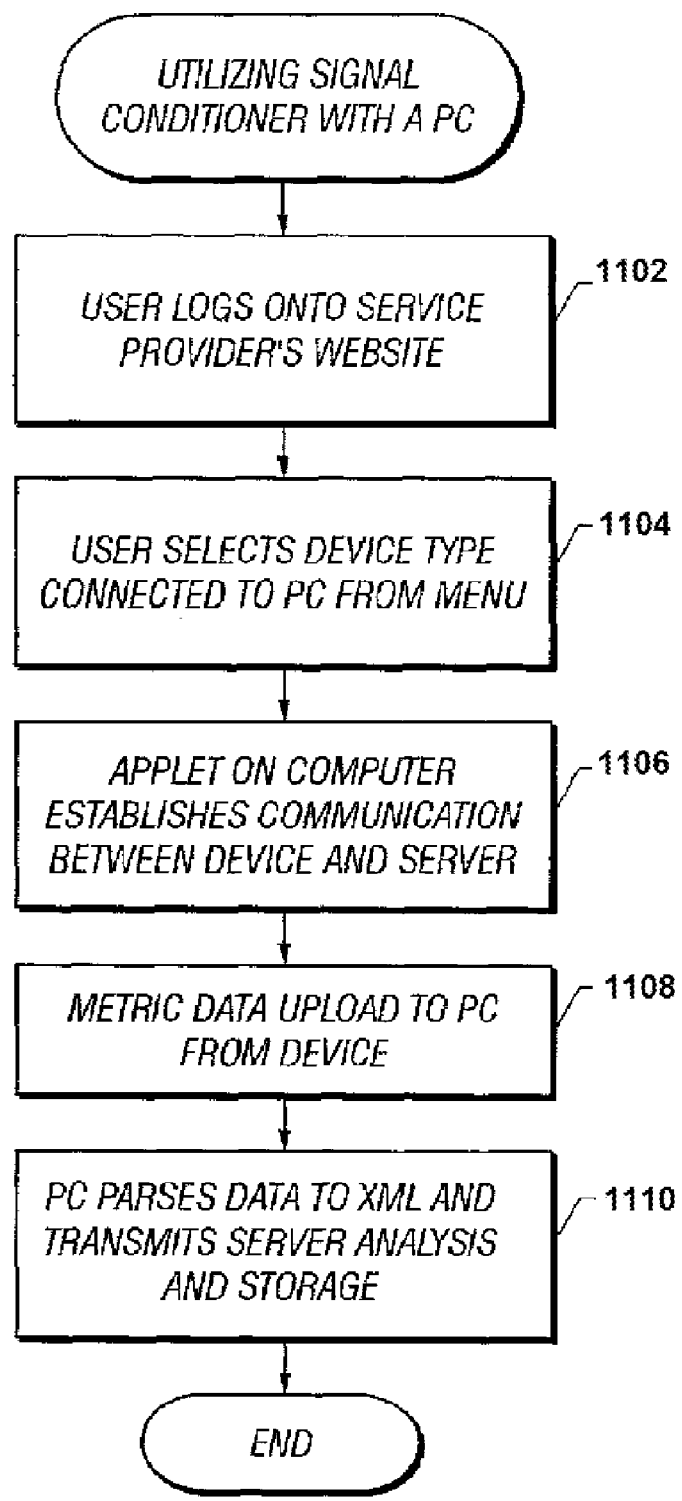
FIG. 11 is a flow diagram of a process of utilizing the signal conditioner with a personal computer to upload metric data to a server in accordance with one embodiment of the present invention.

FIG. 11 is a flow diagram of a process of utilizing the signal conditioner with a personal computer to upload metric data to a server in accordance with one embodiment of the present invention. At step 1102 a health care consumer logs onto the service provider web site using a computer or Internet appliance. The consumer healthcare-taker will have access to a personal health profile that contains health and wellness data that has been collected about the user. It is assumed that the service provider has some information about the user, such as which self-monitoring devices the user is likely to utilize. At step 1104 the user opens a pull-down menu or other type of menu from which the user can choose the type of device that is connected to the computer. Such a menu would normally be customized to the user. At step 1106, an applet on the computer provided by the service provider establishes communication between the device and the server. The applet used to establish this communication depends on the type of self-monitoring device and associated protocol used by the device. Thus, a computer may have several different applets depending on the number of devices used by the consumer. At step 1108 the user invokes the metric data upload or data dump wherein the device transmits all its data to the computer. At step 1110 the computer parses the metric data into XML form and transmits the data to the server where the data is analyzed and stored in the user's health profile.

A signal conditioner can also be used in the computer configuration model. The modification made is that the menu at step 1104 includes the option to use the signal conditioner instead of selecting the self-monitoring device directly. The signal conditioner is then used to collect the data from the device as described above and the data is then transmitted to the computer from where it is uploaded to the server.

Figure 12:
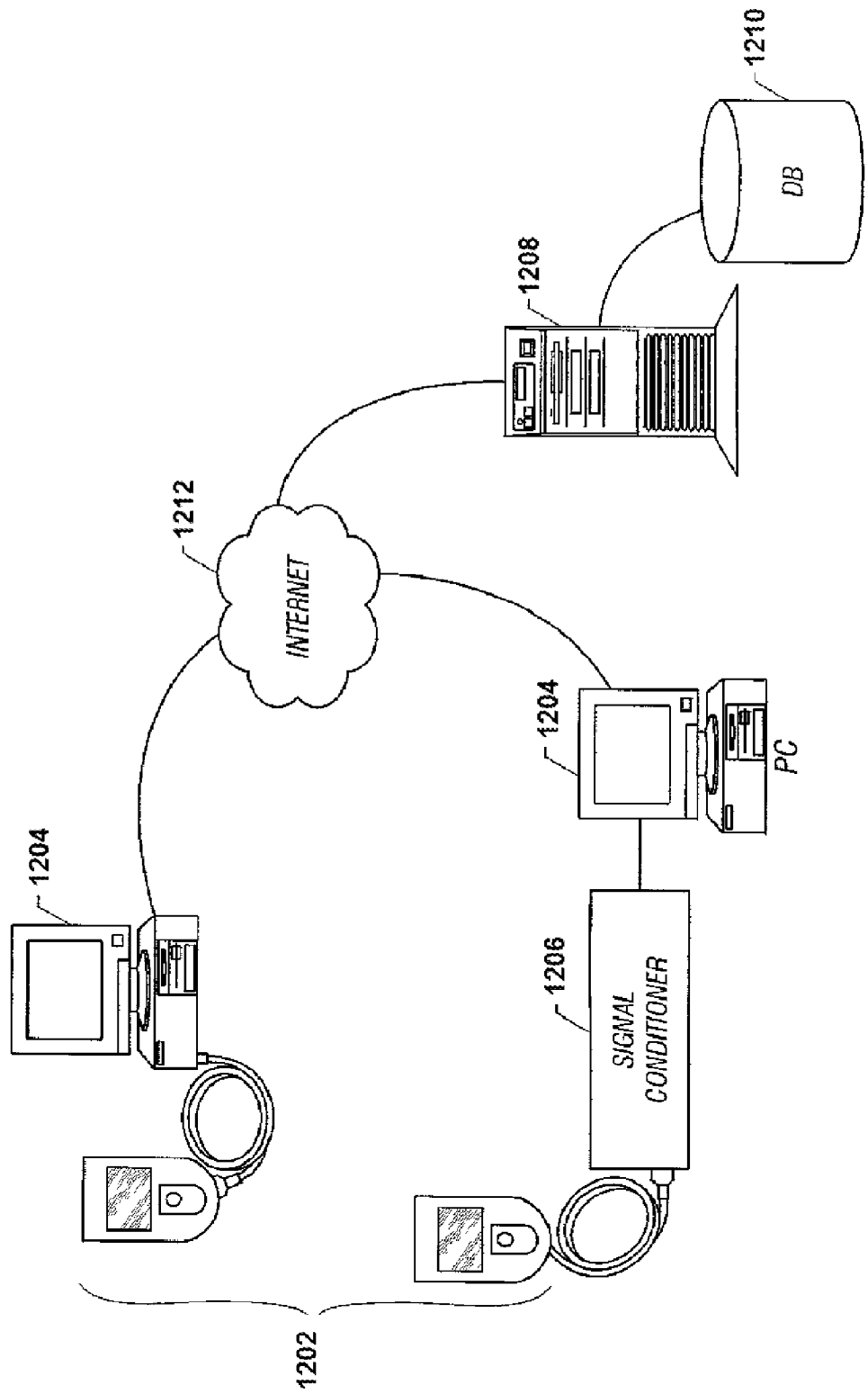
FIG. 12 is a block diagram showing two computer-based configurations for transmitting metric data to a service provider server in accordance with one embodiment of the present invention.

FIG. 12 is a block diagram showing both configurations. In the configuration described in FIG. 11, a self-monitoring device 1202 is connected directly to a PC 604. In a preferred configuration, device 1202 is connected to a signal conditioner 1206. A self-monitoring device 1202 is connected to a signal conditioner 1206 in a manner described above. The host I/O component of signal conditioner 1206 is then connected directly to a serial port of computer 1204 instead of going directly to a phone line. From computer 1204 data is uploaded to server 1208 via the Internet 1212 and modem bank 707. From server 1208 the metric data is downloaded to database 1210." [U.S. Pat. No. 7,375,647 column 3, line 47 to column 6, line 52]

Figure Legends

MetrikLink® intermediate data linking device allows for seamless uploading of data readings from a wide range of self-monitoring health devices to personal health records stored by the service provider and utilizes novel point-of-care technology. A doctor or other healthcare professional may also transmit data to patient health records via the MediCompass® online healthcare data management program system.

Typically, doctors will use MetrikLink® intermediate data linking device in their offices to upload data during office visits when patients bring their disparate and various personal health monitoring devices to their offices. Data is received by the service provider via MediCompass® online healthcare data management program servers and is stored in personal health records so that the data can be uniformly viewed by all authorized entities and is secured in the MediCompass® online healthcare data management program database.

The website screens and a personal health record are further described in the following figures. FIG. 2A is a screen display of a homepage of an online chronic care data management program in accordance with one embodiment of the present invention. On the left side of the display are login fields 202 for patients and on the right side are login fields 204 for professionals. A user can also invoke one of the tabs 206 for information on the service provider, from whom a party initially obtains a login name and password.

A streamlined process of enrolling or registering a patient and doctor in the MediCompass® online healthcare data management program system is described below.

Figure 2C:
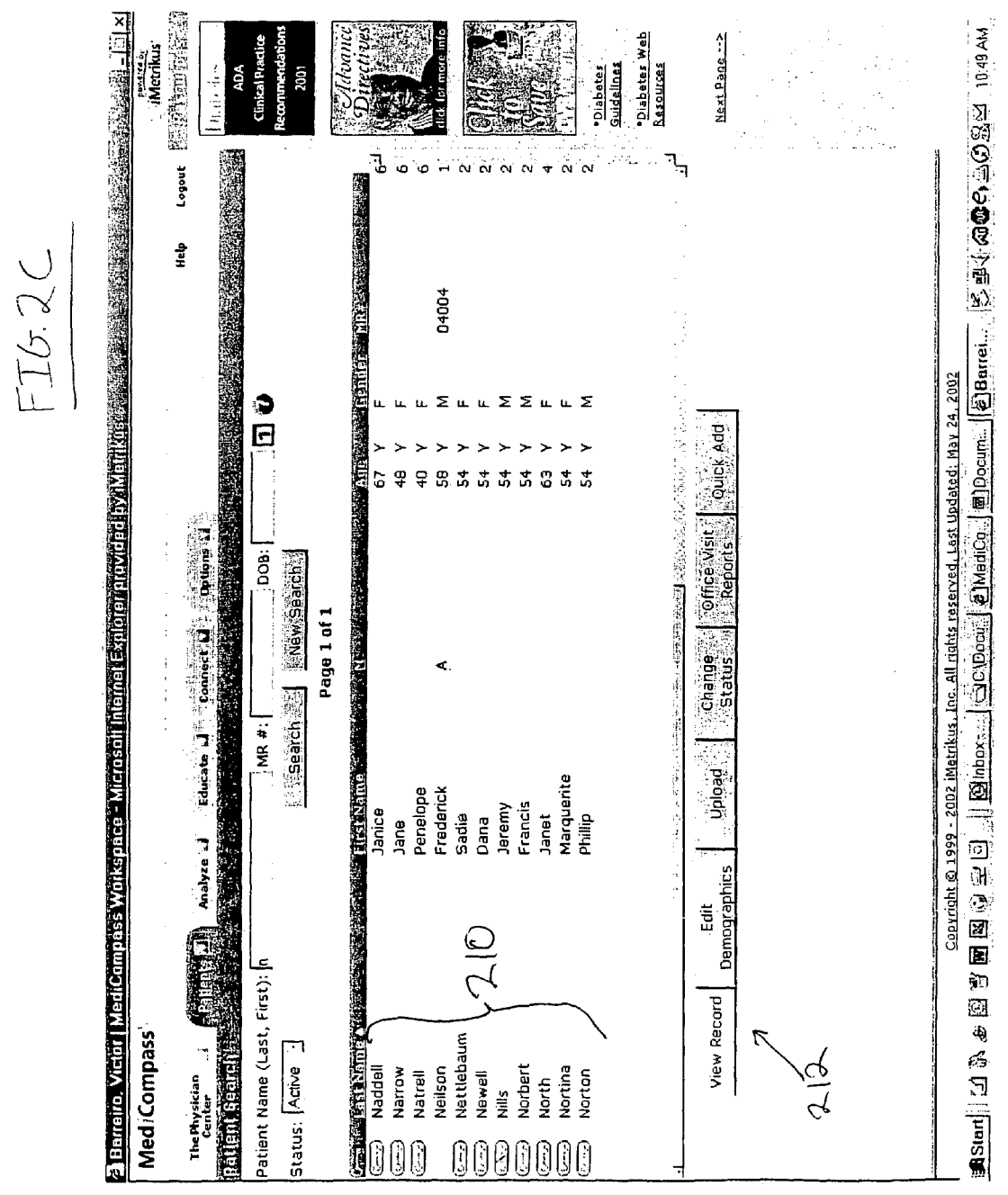

FIG. 2B is a screen display showing a healthcare provider's initial screen, referred to as "MyPracticeCenter" in the described embodiment. MyPracticeCenter is also the first tab of tabs 206 shown in FIG. 2A. The screen display of FIG. 2B is segmented into various sections: "How to Navigate", "New and Notable", "Health News", etc. By selecting the "Patients" tab 208 at the top of the screen display, a doctor enters the screen display shown in FIG. 2C. Here a doctor can search for a patient from a list of patients 210 who have granted the doctor authority to view their record. The doctor can also perform one of a number of activities 212 such as "Add Patient", "View Record" or "Edit Demographics" as displayed below patient list 210. Other healthcare professionals have generally the same screens as the doctor if granted authority by the patient. Some of the screens may be modified to suit the professional's specific needs. For example, a pharmacist may have access to functions that are not relevant to a nurse or lab technician.

By selecting "View Record" for a particular personal health record, a doctor is presented with a screen display shown in FIG. 2D displaying a portion of the information from a personal health record, referred to as "Patient Profile" in the described embodiment. A large portion of data in a health record is general and not necessarily tied to a specific chronic condition being monitored, e.g., diabetes, asthma, cardiovascular disease. These general data include allergies, vitals, medications, and so on. Other data are more specific to the condition, such as HbA1c and blood glucose results (diabetes) or PEV and FEV-1 values (asthma).

FIG. 2E is a screen display showing a patient's meter readings from a glucose meter, as well as time, data, and time slot. The usefulness and benefits to all parties derived from maintaining a personal health record depend on the frequency with which data in the record are updated and whether the patient complies with the treatment strategy established by the healthcare team and reflected in the personal health record.

FIG. 3A is the initial screen on the patient side of MediCompass® online healthcare data management program in accordance with one embodiment of the present invention. Referred to as "MyHealthCenter" in the described embodiment, and similar in format to the "MyPracticeCenter," a patient can view information such as tasks, news, and resources. At the top of the display are tabs 300 allowing the patient to view his personal health record, graphs, reports, and so on. FIG. 3B shows the same screen display with a window 302 which, when a patient is ready to upload data from a monitoring device to his personal health record, allows the patient to select a self-monitoring device by a particular manufacturer. The selected self-monitoring device is connected to the intermediate data linking device, MetrikLink® intermediate data linking device in the described embodiment, to transmit readings to the patient's personal health record stored by the service provider. The screens displaying the patient's health data record are similar or the same as those shown in FIGS. 2D and 2E for healthcare professionals.

It is evident that the platform and methods of the present invention for improved collaboration and point-of-care communication between patients and healthcare professionals depend on having entities joining the network, wherein the network comprises one aspect of the online chronic care data management program referred to generally in the described embodiment as MediCompass® online healthcare data management program.

One feature of the online care management program is that it encourages self-management of chronic and non-chronic conditions by following a treatment strategy. Another feature is that it enables a healthcare team and other third-parties to monitor patient compliance with the treatment strategy. That is, the patient, his healthcare team, and other authorized parties can monitor how well a patient is following all aspects of a prescribed treatment strategy, such as exercise, diet, medication, self-testing, and so on. In addition, MediCompass® online healthcare data management program allows a party to track what products and pharmaceuticals are purchased by a patient using the online program. Therefore, it would be desirable to facilitate the process in which patients and doctors join MediCompass® online healthcare data management program and to provide incentives to patients to frequently update personal health records and comply with treatment strategies.

Often a notable barrier to joining an online network and platform, such as MediCompass® online healthcare data management program, is the significant initial investment of resources and time needed to upload patient data and install the technology for accessing the network. Generally, individuals and organizations are less willing and motivated to join online networks if the initial effort and costs required to do so are too high or prohibitive. In the context of the present invention, even if a patient is persuaded to join, it is unlikely that the patient will attempt to persuade his doctor and other members of his healthcare team to also join the network. It would be preferable if doctors recommended and motivated patients to join the network.

Thus, an effective model of the present invention involves a healthcare professional informing his patients of the MediCompass® online healthcare data management program network and providing the patient with the materials needed to join the network in a manner in which time and costs are minimized for all parties. Similarly, the model allows clinics, already burdened with increasing costs and reduced resources, to join the MediCompass® online healthcare data management program network without expending significant time and resources. For example, the methods of the present invention for joining the online health data management network require minimal paperwork and expense. Furthermore, the initial time required by a doctor to enter participating patients into the network is reduced as much as possible. In a preferred embodiment, doctors do not manually input information for all existing patients into MediCompass® online healthcare data management program. This is a significant factor for a clinic if the number of patients is in the hundreds or thousands. In the present invention, the healthcare data service provider, the party operating the MediCompass® online healthcare data management program system and enabling MetrikLink® intermediate data linking device, is in a position to facilitate the processes for patients to join the network.

To illustrate the methods and platform of the present invention, it would be helpful to use as an example a diabetes clinic having several doctors, a high volume of patients, and a business relationship with a particular drug company. The drug company has informed the clinic, also referred to as a practice site, of the drug company's sponsored MediCompass® online healthcare data management program, and has given the clinic an opportunity to participate.

The practice site is informed of the numerous benefits of doing so. First, by joining MediCompass® online healthcare data management program, the clinic will start on a path to replacing the multiple software programs it presently needs to receive and process data from the multiple devices its patients are using, such as blood glucose meters and insulin pumps, with a single software program and interface. By participating, patients can update their health records online or, if a computer is not available or accessible, use MetrikLink with their particular home monitoring device to transmit data to their personal health record. Doctors can use the MediCompass® online healthcare data management program interface to view, access, and process data stored in the patient's personal health record.

This effectively eliminates the need for the clinic to maintain multiple software programs and interfaces for each type of self-monitoring device used by its patients. It also eliminates having numerous disparate databases storing patient data and readings from the various meters. Other benefits to joining MediCompass® online healthcare data management program include branding and marketing opportunities for other entities in the healthcare industry, such as pharmaceutical, life science, medical device companies, and financial and insurance companies, that have a business relationship with the clinic. Moreover, the network encourages collaboration between patients and doctors and increased involvement by the patient in the monitoring and treatment of his condition.

Once the clinic has decided to utilize MediCompass® online healthcare data management program, it works closely with the service provider, although the work it has to do to get started is minimized. The service provider operates the engines and servers that power the network and maintains personal health record data. As described in FIG. 1, all personal health data is stored by the service provider and is not transmitted to any other entity. For example, the doctor accesses the server via the web and views the patient's data residing on the server.

In a preferred embodiment, a doctor selects a patient from a list of patients who have joined MediCompass® online healthcare data management program and have granted him access to their records. Similarly, a patient can select which doctors or other healthcare professionals associated with a practice site will be authorized to share access to his health data. For example, a patient may have a number of professionals in his healthcare team, such as a primary care physician, a specialist, a nurse, a pharmacist, and others. When registering for the service, the patient can select which practice site and participating healthcare professionals may view the data. In the described embodiment, the view of a patient's personal health record data available to patients and healthcare professionals on MediCompass® online healthcare data management program is, to a large extent, the same.

A personal health record contains health and wellness data and other information useful to doctors and other healthcare professionals. A health record also enables a patient to collaborate with his doctor for better healthcare management and to get more involved in his treatment strategy. As such, a personal health record is intended to be viewed by numerous parties authorized by the patient; its value derives from it being used by the patient and his healthcare team. It is distinguishable from an electronic medical record in that an EMR is maintained strictly by a healthcare professional, mostly doctors or specialists, for medical and legal purposes, and is not intended to be shared with or viewed by the patient. A personal health record of the present invention essentially contains communications between a patient and his healthcare professionals, personal health and wellness data entered by the patient or professional, and readings from self-monitoring devices. MediCompass® online healthcare data management program is the channel through which the parties collaborate. It is this new method and form of communication between patients and their doctors that enable collaboration between the parties and is designed to encourage a patient to improve his chronic health conditions through self-management, thus reducing healthcare costs over time.

Although the foregoing description of the present invention has emphasized patients uploading data—primarily readings and measurements from home self-monitoring devices—to the patient's personal health records, it is important to keep in mind that the system can be used by doctors and other healthcare professionals, including the service provider, to transmit or "push" various types of information to patients. For example, a doctor can broadcast a general message to all her diabetes patients, to a subset of her patients, or to a specific patient. For example, the message can contain information on the latest developments in treatment, a reminder to make an appointment, or an instruction or alert regarding medication. More generally, the platform can use demographic information, such as geographic location, birthdate, and so on, as well as a patient's clinical data to display information relevant to his condition on the patient's MyHealthCenter page.

In a preferred embodiment, a doctor can place messages in a queue and have the messages transmitted at designated times, e.g., a reminder to take a critical medication. The messages can be of various types, ranging from health news relevant to the patient to tasks that the patient needs to complete. In a preferred embodiment, a patient's demographic and clinical data can be used to drive content to the patient on MediCompass® online healthcare data management program. All forms of communication between patients and doctors and other healthcare professionals, particularly when the communication is tailored for a particular patient, improves collaboration between patients and doctors.

Figure 4A:
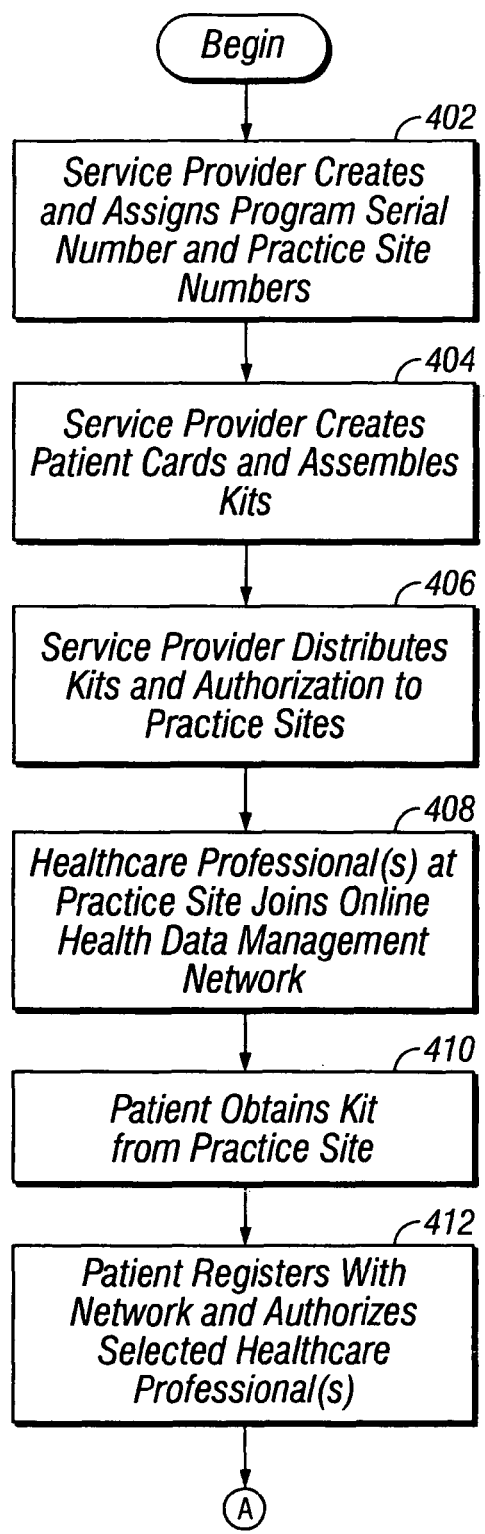
FIGS. 4A and 4B are flow diagrams of a process of storing patient data in a network and distributing a patient membership card and other information needed for joining an online chronic care data management network in accordance with one embodiment of the present invention.
Figure 4B:
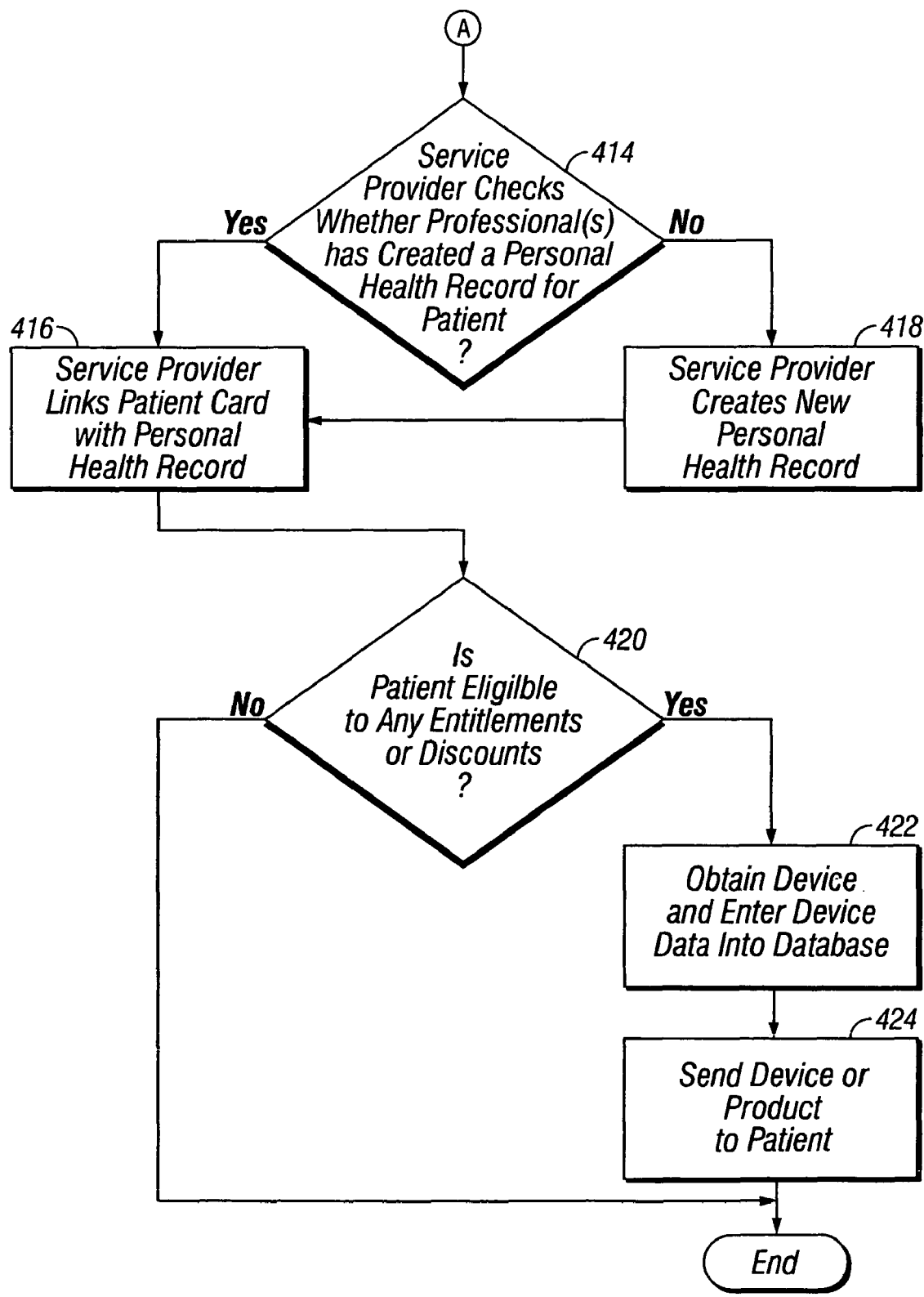

FIGS. 4A and 4B are flow diagrams of a process of storing patient data in a network and distributing a patient membership card and other information needed for joining the network in accordance with one embodiment of the present invention. The service provider is the creator and originator of the necessary components for joining the network and may, in some embodiments, have the task of entering the relevant information into the MediCompass® online healthcare data management program system. In the described embodiment, the service provider assigns patient membership cards—one of the components for joining the network—referred to as a MediCompass Card® patient membership card described in greater detail below. Cards are assigned in the MediCompass® online healthcare data management program database to the practice site.

In a preferred embodiment, another party involved in the process which has not been described at detail above is a third-party company which actually initiates and drives the process of enrolling individuals in MediCompass® online healthcare data management program. Essentially, in the described embodiment, this third-party company provides the initial motivation for doctors and patients to enroll in the network. The third-party company is typically a large healthcare company, such as a pharmaceutical or life sciences company or health insurance company. In the diabetes clinic example, the third-party company may be the drug company that has an existing relationship with the clinic. Typically, the third-party company has a product, service, or program which it wants to promote and/or sell to entities that provide healthcare services directly to patients, such as clinics, hospitals, medical groups, individual doctors, and so on.

In a preferred embodiment, at the outset, the service provider implementing and managing MediCompass® online healthcare data management program collaborates with the third-party company. By partnering with the service provider, the third-party company can obtain valuable depersonalized data relating to compliance patterns, status changes, and opportunities for intervention. Furthermore, the company can benefit from branding opportunities, gathering valuable consumer data, building name recognition and goodwill, promoting and selling its products or services, and demonstrating product efficacy, among other benefits. The data captured by the service provider can be mined for the benefit of the third-party company. For example, the data can be mined for specific data relating to usage patterns, prescribing behaviors, treatment strategy compliance, and therapeutic goal achievement. In the described embodiment, relationships between products and therapeutic results are continuously documented and made available to the third-party company through various types of aggregate reporting or targeted reporting, e.g., when a threshold or parameter relating to patient activity or condition is reached or exceeded.

To illustrate, assume the third-party, a drug company, sells its medication to 80 practice sites and would like to increase its market share and goodwill amongst those sites, specifically amongst patients and doctors at those sites. It would also like to collect consumer data and offer incentives and discounts to those patients and practice sites. The drug company partners with the service provider to achieve these goals. The company also knows that in the process it is enabling improved communication and collaboration between patients and healthcare professionals. By doing so, it is creating brand recognition and goodwill in the minds of patients and healthcare professionals.

As a preliminary step, the company has informed the service provider that there are presently 80 practice sites which the company would like to authorize for the MediCompass® online healthcare data management program. Once the drug company and service provider have reached an agreement for implementing a program, the process of signing up patients, doctors, and healthcare professionals begins.

At step 402 of FIG. 4A, the service provider creates and assigns a program serial number that specifically identifies a program sponsored by the third-party company. A third-party company, such as the drug company, may have more than one program with the service provider, in which case each program will have its own program serial number. For example, a specific program may have Ser. No. 00/012,231. At step 402 the service provider associates practice sites with the program sponsored by the drug company. The drug company may also inform the service provider of how many patient membership kits and cards each practice site should receive.

In a preferred embodiment, a membership kit is distributed to patients. The kit contains a patient membership card, referred to as a MediCompass Card® patient membership card in the described embodiment, that contains information on the program being sponsored by the drug company, instructions for joining MediCompass® online healthcare data management program (both for those who choose to do so online as well as instructions for those who choose not to use the Internet or are unable to do so), information on entitlement to free products, devices (such as a MetrikLink® intermediate data linking device or AirWatch® personal respiratory monitor device), or services, and/or discounts on other products. In a described embodiment, the packaging of the kit and the materials in the kit, particularly the patient membership card, can display trademarks, names, slogans, etc. of the drug company, so that it appears to the patient that the service is being provided by the drug company.

Thus, at the end of step 402, the service provider has sufficient information to create a sponsored program, assign patient membership cards, and associate the card with a specific practice site, using a unique card serial number. In the described embodiment, the unique serial number is encoded on the card in a machine-readable format, such as a bar code.

Figure 6A:
FIGS. 6A and 6B show the front and back of a sample patient membership card in accordance with one embodiment of the present invention.
Figure 6B:

FIGS. 6A and 6B show the front and back of a sample patient membership card in accordance with one embodiment of the present invention. The figures show a human readable identifier "000 109 9E4K" and bar code encoding the unique card number.

At step 404 the service provider manufactures the patient membership cards and assembles the kits containing the cards and other materials for the specific sponsored program. As noted, the appearance and packaging of the patient membership cards and kits can be customized as instructed by the sponsoring drug company.

At step 406 the service provider distributes the kits to the 80 specified practice sites. In the described embodiment, the drug company has compensated the service provider for creating the cards and kits, distributing the kits to the practice sites, and for administering the MediCompass® online healthcare data management program on behalf of the drug company. The company has informed the service provider that it would like the practice sites and their patients to be members of MediCompass® online healthcare data management program and has provided some form of compensation to the service provider for the membership of these 80 practice sites, its patients, and for management of the program.

Thus, at the end of step 406, each of the selected sites has received authorization and instructions for joining MediCompass® online healthcare data management program and kits for distribution to patients. Presumably, before this, either the drug company or the service provider has informed each of the practice sites that the site has been authorized to join MediCompass® online healthcare data management program and that it will be receiving MediCompass® online healthcare data management program instructions and a certain number of patient kits. In the process, it is recommended to the doctors and other professionals at the practice site that they join MediCompass® online healthcare data management program. The service provider makes training services and training materials available to the practice sites when necessary.

At step 408 an individual at the participating practice site, such as a doctor or other healthcare professional, joins MediCompass® online healthcare data management program. In the described embodiment, membership in the online health data management program is attained at the individual level. Thus, one or more doctors or professionals at a practice site will join MediCompass® online healthcare data management program. For example, Westside Clinic, a practice site that recently began prescribing the drug company's medication and one of the sites selected by the drug company to be in the program, has received 100 patient kits. To further illustrate, Westside Clinic also prescribes similar medication manufactured by one of the drug company's competitors. The drug company sponsoring the program would like to increase its business with Westside Clinic and build greater brand recognition and goodwill amongst its patients. One of the numerous ways the drug company can build brand recognition and goodwill is by placing its name and trademark on the patient membership card shown in FIGS. 6A and 6B, and on the kit packaging.

At step 408, an employee at the practice site, such as an administrator or IT professional, enrolls each of the doctors and other healthcare professionals at the clinic who wants to join MediCompass® online healthcare data management program into the network. This can be done either online, by fax, or by telephone. In another preferred embodiment, the practice site can contact the drug company and request that the drug company enroll the doctors and professionals at the site in MediCompass® online healthcare data management program, although there are certain steps that need to be taken at the practice site, such as preparing the computer, selecting passwords, and so on. One of the objectives of the present invention is to minimize the steps and time required of the practice sites and patients to join MediCompass® online healthcare data management program.

At step 410 of FIG. 4B, patients pick up the kits when they visit the practice site. In the described embodiment, a patient obtains a kit during an office visit. In another preferred embodiment, the kits are mailed to the patients. A patient joins MediCompass® online healthcare data management program by calling the service provider customer support to activate their membership based on the membership number on the MediCompass Card within the kit. The kit may also contain an entitlement or discount to a MetrikLink® intermediate data linking device or other device or product, such as one manufactured by the sponsoring company. In another preferred embodiment, the kit includes one or more devices so the patient may begin uploading data to the MediCompass® online healthcare data management program database immediately after registering with MediCompass® online healthcare data management program.

Recall that a patient membership card already has identifiers associating it with the specific program (and thus the sponsoring company) and the practice site. At step 412 the patient registers with the online health management program. In the described embodiment, when the patient registers with MediCompass® online healthcare data management program he specifies one or more doctors and professionals at the practice site where he obtained the card who he grants authority to access the patient's personal health record. These individuals now have permission to collaborate with the patient through MediCompass® online healthcare data management program.

A patient activates his membership in the network via the Internet by calling a customer support number maintained by the service provider. The patient provides personal and demographic information to the service provider, such as name, address, birth date, primary health, condition to be monitored, and security questions/answers for subsequent identification when calling customer support. In a preferred embodiment, this information is used for initially creating a personal health record. A personal health record is subsequently populated with clinical data, device readings, medication data, data specific to the patient's chronic condition, and a wide range of other health and wellness information, mostly supplied by the patient. As mentioned above, the patient also identifies which professionals will have access to the patient's personal health record.

Thus, at the end of step 412 a patient has joined MediCompass® online healthcare data management program and has provided information needed for creating a personal health record. The patient has also informed the service provider which professionals at the practice site will have access to the patient's personal health record.

At step 414 the service provider checks whether the doctor specified by the patient at step 412 has already created personal health record for the patient. A doctor is not required at any time to create a personal health record for each of her patients. However, a doctor or other healthcare professional may choose to create an initial personal health record for her patients before they pick up the kit or at the time the kit is picked up. On the other hand, the doctor can shift this task to the service provider and patient.

If the service provider determines at step 414 that the doctor has already created a personal health record for the patient, the service provider links the card number uniquely identifying the card with the existing personal health record at step 416. The patient reads the number from the card. The bar code is used by the service provider internally before the cards are shipped to practice sites. If there is no match at step 414, at step 418 the service provider creates a new personal health record for the patient and inserts the patient name in the list of patients for the one or more healthcare professionals specified by the patient.

Once a personal health record has been created at step 418, control returns to step 416 where the service provider couples the patient membership card number with the newly created personal health record.

At step 420 the service provider examines the program serial number and practice site serial number to determine if the patient has any entitlements or discounts to products. For example, a patient may be entitled to a discount on a MetrikLink® intermediate data linking device, AirWatch® personal respiratory monitor device, or other product from the service provider or sponsoring company, or may be entitled to a free product or service.

If the service provider determines at step 420 that the patient has an entitlement to a particular device, at step 422 of FIG. 4C the service provider retrieves a new device and enters the device serial number into the patient's record in the MediCompass® online healthcare data management program database. Before or at the time the device is shipped to the patient, the serial number for the device is associated or linked with the patient's personal health record. As described below, by making this association between device and health record, the service provider can efficiently and seamlessly update the appropriate personal health record in the MediCompass® online healthcare data management program database when it receives device readings via the telephone lines.

At step 424 the device is sent to the patient by the service provider or other appropriate party upon instructions from the service provider. At this stage, the process of creating a personal health record and entering the patient as a member of MediCompass® online healthcare data management program is complete. If there are no entitlements, the process of entering the patient into the network and of creating a personal health record for the patient is complete. If desired, the patient can go to the MediCompass® online healthcare data management program website, click on First Time Users, and register for online access to the personal health record that has been created for them. Although encouraged by the service provider, sponsoring company, and professionals, the patient need not access the personal health record online. This may be the case where a patient simply wants to upload readings from home monitoring devices so his healthcare team can examine them. In such cases, the patient may not have any need or desire to maintain a more complete personal health record. On the other hand, in addition to uploading meter readings, a patient may use his personal health record for keeping a wide variety of wellness, health, and medical data and may wish to access it daily.

In the present invention, the key set of data is the personal health record. From a broad perspective, the personal health record provides a snap shot of how the patient is progressing with his prescribed treatment strategy or, in cases where there is no specific strategy, how the patient's health is improving generally. In addition to showing how the patient is doing, the personal health record can also show how well the patient is complying with a treatment strategy and whether the patient is complying with specific instructions from his healthcare team. There is a wide range of sample indicators that can be used to rate compliance: frequency of downloaded device readings, medication intake, following an exercise regimen, sticking to a diet, and other health and wellness indicators. These and many other activities and readings can be measured and tracked in a personal health record maintained by MediCompass® online healthcare data management program.

For this and other reasons, it is desirable to keep a personal health record accurate, current, and data rich by updating the record as often as possible. One way to facilitate reaching these goals is to streamline and simplify the processes of updating a health record.

Figure 5:
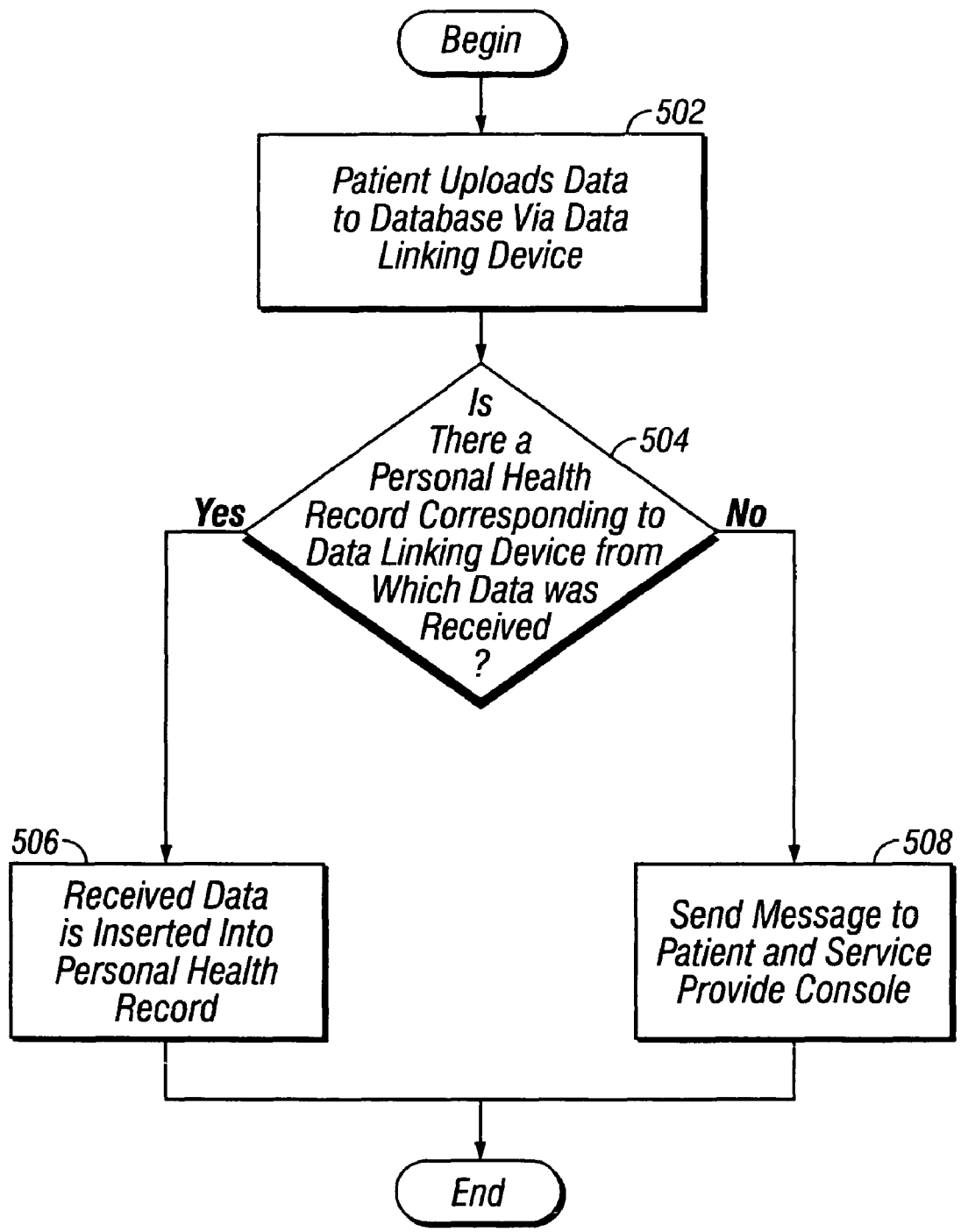
FIG. 5 is a flow diagram showing a process in which a patient updates a personal health record with device readings in accordance with one embodiment of the present invention.

FIG. 5 is a flow diagram showing a process in which a patient updates a personal health record with device readings in accordance with one embodiment of the present invention. The patient is able to share health information with his doctor in a novel manner. Similarly, a doctor is able to communicate with his patient in ways and formats previously unavailable. At step 502 a patient uploads data from an intermediate data linking device, such as MetrikLink® intermediate data linking device, to secure databases maintained by the service provider. The patient does this by connecting a self-monitoring device such as a glucose meter to a data linking device, and connecting, the linking device to a computer or other Internet-enabled device.

However, it may not be convenient for the patient to use a computer each time he wants to upload data. As noted above and described in the MetrikLink patent application referenced above and incorporated herein, the data can also be transmitted directly to the service provider without the use of a computer. The intermediate data linking device can be connected directly to MediCompass® online healthcare data management program via a telephone outlet. When a computer is used to send the data, the patient can include personal health and wellness information in addition to readings and other data from self-monitoring devices.

When using an intermediate data-linking device, and connecting through a phone outlet to transmit data to MediCompass® online healthcare data management program, the data includes, in addition to the meter readings, the unique serial number of the device. This serial number identifies the patient. This is possible because the intermediate data linking device sending the data to MediCompass® online healthcare data management program has already been associated with the patient at step 408 of FIG. 4A. In a preferred embodiment, the device serial number is contained in a header of the data transmitted to the MediCompass® online healthcare data management program database.

At step 504 the MediCompass® online healthcare data management program database receives the data over the network and searches for the intermediate data linking device serial number in the data stream. The MediCompass® online healthcare data management program engines use the device serial number to search the personal health record database for a corresponding health record. Each personal health record has a field storing a device serial number, e.g., a MetrikLink® intermediate data linking device number, written to the record by the service provider at step 416 of FIG. 4B. If a personal health record is identified, the record is retrieved and the data is inserted into the record at step 506 and the process of updating a personal health record by a patient is complete. If a personal health record cannot be identified based on the device serial number, at step 508 an appropriate message is sent to the patient, such as via an LED or LCD display on the device. This would occur, for example, if the device were not properly registered with the service provider by the patient.

As noted above, it is important for the online health data management program, in the described embodiment MediCompass® online healthcare data management program, that the personal health records be kept current for the management program to be most effective in managing chronic health conditions. The over-arching goal of the present invention is improving the health of patients, particularly those having chronic conditions or conditions that require close monitoring, while reducing healthcare costs through the collection and study of aggregate data.

For patients having chronic health conditions, healthcare costs run high. By complying with a health treatment strategy and with specific instructions from a healthcare team, a patient is more likely to improve his condition. This benefits not only the patient, but other entities in the healthcare industry such as insurance and pharmaceutical companies (e.g., providing an opportunity to establish the efficacy of a new drug). An additional incentive for patients to comply with a treatment strategy and fully utilize a personal health record is to be rewarded for meeting and exceeding thresholds established by the patient's healthcare team.

For example, a doctor may determine that if a patient took a certain medication three times daily, exercised five times a week, and took readings from a self-monitoring device at least twice daily enabling closer monitoring by the healthcare team, his lab results and likewise his condition would likely improve over time. The online health data management program of the present invention tracks a patient's activities using the personal health record and, using techniques well known in the field of software programming, can detect when a threshold value is met or exceeded. For example, if the management program detects a second device reading within a 24-hour period, the program can send a message to a relevant party or increment the number of credits or points for that patient. In another example, a patient may be taking medication from a particular pharmaceutical company three times daily as established by a treatment strategy. Staying within the ambit of applicable regulations and privacy laws, such activity may be reported as a depersonalized aggregate summary to the pharmaceutical company.

In a preferred embodiment, patient utilization and behavior that complies with or exceeds a treatment strategy set by a healthcare professional (and reflected in the patient's personal health record) entitles the patient to points or credit that can be used by the patient to obtain a benefit that the patient values. Such benefits can vary widely, ranging from discounts on medical devices, medication, exercise equipment, insurance premiums, reductions in deductibles, and other health and wellness related benefits. In another preferred embodiment, the patient can obtain benefits not related to health and wellness. Such benefits are limited only by the type of third-party companies that partner with the service provider and what they have to offer patients. The more frequently a patient complies with a treatment strategy, the more points the patient collects over time. The patient is also rewarded when she purchases or uses products from a third-party company that has partnered with the service provider. With significant increases in healthcare costs, particularly costs related to chronic health conditions, earning "compliance points" can provide a strong incentive to follow a treatment strategy and fully utilize the personal health record of the present invention.

A patient receives a MediCompass® online healthcare data management program kit when visiting a practice site. In the described embodiment, the kit contains instructions on how the patient can join MediCompass® online healthcare data management program and a patient membership card. By picking up the kit at the doctor's office, the expense and time of mailing the kit to patients are avoided. The patient is informed that data readings from numerous types of self-monitoring medical devices can be uploaded to a personal health record regardless of whether the patient has Internet access. Even if the patient does have Internet access, he may prefer using MetrikLink® intermediate data linking device to eliminate the need to log in and to save time when only uploading his device readings. The option of not using a computer may be greatly beneficial to certain demographic groups of patients, such as the elderly, lower income patients, patients who travel frequently, and physically disabled patients. These groups may have difficulty or find it inconvenient to get online using a computer each time they wish to upload readings to the database.

Methods of creating an online personal health record of the present invention and motivating patients, doctors, and healthcare professionals to join the network are novel in that they take into account the workload and available resources of the patient and the healthcare professional. In the described embodiment, MediCompass® online healthcare data management program allows doctors to view an updated personal health record of a patient without having to contact the patient using conventional means, e.g., telephone, written correspondence, office visits, and so on, thereby extending the reach and enhancing the relationship between doctors and their patients. Recall that personal health records are intended to be primarily maintained by patients, in contrast to an EMR, and thus do not significantly increase the workload of the doctor or other healthcare professionals, yet provides access to a wealth of personal health data. The personal health record and the online health data management program also empower the patient to take a more proactive role in monitoring his chronic health conditions and collaborating with his healthcare professional to improve his health.

In a preferred embodiment, a doctor has the capability in MediCompass® online healthcare data management program to print a patient's personal health record as a report in a format specified by the doctor. This is important because many doctors may not want to read patient data on a computer screen and, rather, may simply want to review printed reports of health records on a regular basis. In another preferred embodiment, the service provider can print reports of personal health records for a particular doctor and mail the reports to the doctor. The doctor can specify that she wants certain aggregate data formatted in a particular manner. The dissemination of the report data to the doctor can occur in numerous ways, for example, as a fax or a report printed on a printer in the doctor's office. In addition, the present invention provides a high level of privacy and security. Finally, the present invention attracts and retains motivated patients who seek a comprehensive and meaningful way to better manage their health conditions.

Although the foregoing invention has been described in some detail for purposes of clarity of understanding, it will be apparent that certain changes and modifications may be practiced within the scope of the appended claims. Furthermore, it should be noted that there are alternative ways of implementing both the methods and systems of the present invention. For example, a MetrikLink® intermediate data linking device is not required to send data to the MediCompass® online healthcare data management program database. Data may be transmitted directly from a personal health monitoring device into a patient's MediCompass® online healthcare data management program record using a computer and device serial cable. Or, data can be entered manually. Accordingly, the present embodiments are to be considered as illustrative and not restrictive, and the invention is not to be limited to the details given herein, but may be modified within the scope and equivalents of the appended claims.

We claim:

1. A method of collaboration between a consumer and a healthcare provider comprising:
   i) connecting a self monitoring device to an intermediate data linking device via a device specific adapter with a specific resistor value;
   ii) dividing the fixed resistor value of the device specific adaptor by the data linking device resistance to produce an analog voltage which identifies a cable type of the self monitoring device;
   iii) using the analog voltage to identify the connected self monitoring device and determining the way health data from the self monitoring device will be transmitted, wherein the data linking device transmits a cable type value corresponding to the cable type to a remote database, and the remote database transmits device configuration instructions, based on the cable type, to the intermediate data linking device to configure a multiplexer in the intermediate device to an appropriate output level and appropriate bit rate to enable communication with the self monitoring device;
   iv) transmitting health data from the self monitoring device to the remote database;
   v) receiving at the remote database the health data from the self monitoring device;
   vi) transmitting a second set of health data to the database, wherein the second set of health data is caused to be transmitted by a provider;
   vi) storing the health data from the health monitoring device and the health data from the provider in a personal health record.

2. The method as recited in claim 1, wherein the personal health record is maintained in the database by a third party.

3. The method as recited in claim 1, further comprising executing an online healthcare data management program to update the personal health record at the database.

4. The method as recited in claim 3, further comprising allowing a healthcare provider to access the personal health record if the consumer has granted authority.

5. The method as recited in claim 4, further comprising enabling the consumer to grant authority to access a personal health record corresponding to the consumer to one or more healthcare providers.

6. A method as recited in claim 1 further comprising pushing data to a consumer, the data originating from a healthcare provider, the data including relevant health data to the consumer.

7. A method of collaboration between a consumer and a healthcare provider comprising:
   i) connecting a self monitoring device to an intermediate data linking device via a device specific adapter with a specific resistor value;
   ii) dividing the fixed resistor value of the device specific adaptor by the data linking device resistance to produce an analog voltage which identifies a cable type of the self monitoring device;
   iii) using the analog voltage to identify the connected self monitoring device and determining the way health data from the self monitoring device will be transmitted;
   wherein the data linking device transmits a cable type value corresponding to the cable type to a remote database, and the remote database transmits device configuration instructions, based on the cable type, to the intermediate data linking device to configure a multiplexer in the intermediate device to an appropriate output level and appropriate bit rate to enable communication with the self monitoring device;
   iv) transmitting health data from the self monitoring device to the remote database;
   v) receiving at the remote database the health data;
   vi) storing the health data in a personal health record in the remote database; and
   vii) examining the health data, stored in the remote database.

8. The method as recited in claim 7, wherein the personal health record is maintained in the remote database by a third party.

9. The method as recited in claim 7, further comprising executing an online healthcare data management program to update the personal health record at the remote database.

10. The method as recited in claim 9, further comprising allowing a healthcare provider to access the personal health record if the consumer has granted authority.

11. The method as recited in claim 10, further comprising enabling the consumer to grant authority to access a personal health record corresponding to the consumer to one or more healthcare providers.

12. The method as recited in claim 7, further comprising pushing data to a consumer, the data originating from a healthcare provider, the data including prompts for the consumer to act, notifications to the consumer of developments relating to a condition, alerts, reminders, and personalized messages.

13. The method as recited in claim 7, further comprising pushing data to a patient, the data based on the patient demographics or on data contained in a corresponding personal health record.

* * * * *